United States Patent
Frangineas, Jr. et al.

(10) Patent No.: US 12,048,851 B2
(45) Date of Patent: Jul. 30, 2024

(54) ALTERNATING HIGH FREQUENCY AND LOW FREQUENCY DUTY CYCLES FOR MUSCLE STIMULATION

(71) Applicant: ZELTIQ Aesthetics, Inc., Pleasanton, CA (US)

(72) Inventors: George Frangineas, Jr., Fremont, CA (US); Theodorus Johannes Virginia Caberg, Eben-Emael (BE)

(73) Assignee: Zeltiq Aesthetics, Inc., North Chicago, IL (US)

( * ) Notice: Subject to any disclaimer, the term of this patent is extended or adjusted under 35 U.S.C. 154(b) by 598 days.

(21) Appl. No.: 17/100,725

(22) Filed: Nov. 20, 2020

(65) Prior Publication Data

US 2021/0146150 A1     May 20, 2021

Related U.S. Application Data

(60) Provisional application No. 62/938,222, filed on Nov. 20, 2019.

(51) Int. Cl.
*A61N 2/00* (2006.01)
*A61N 2/02* (2006.01)

(52) U.S. Cl.
CPC .............. *A61N 2/004* (2013.01); *A61N 2/02* (2013.01)

(58) Field of Classification Search
CPC .................................. A61N 2/004; A61N 2/02
See application file for complete search history.

(56) References Cited

U.S. PATENT DOCUMENTS

| | | | |
|---|---|---|---|
| 10,471,269 | B1 | 11/2019 | Schwarz |
| 10,478,634 | B2 | 11/2019 | Schwarz et al. |
| 10,493,293 | B2 | 12/2019 | Schwarz et al. |
| 10,556,122 | B1 | 2/2020 | Schwarz et al. |
| 10,632,321 | B2 | 4/2020 | Schwarz et al. |
| 10,688,310 | B2 | 6/2020 | Schwarz et al. |
| 10,695,575 | B1 | 6/2020 | Schwarz et al. |
| 10,695,576 | B2 | 6/2020 | Schwarz et al. |
| 10,709,894 | B2 | 7/2020 | Schwarz et al. |
| 10,709,895 | B2 | 7/2020 | Schwarz et al. |
| 11,266,852 | B2 | 3/2022 | Schwarz et al. |
| 11,464,994 | B2 | 10/2022 | Schwarz et al. |
| 11,497,925 | B2 | 11/2022 | Schwarz et al. |

(Continued)

FOREIGN PATENT DOCUMENTS

DE     202016008804 U1     10/2019

*Primary Examiner* — Christine H Matthews
(74) *Attorney, Agent, or Firm* — Mintz, Levin, Cohn, Ferris, Glovsky and Popeo, P.C.

(57) ABSTRACT

A method for strengthening, toning, and firming muscle tissues, the method includes receiving parameters for operating a magnetic muscle stimulation device. The parameters include: a first waveform frequency; one or more pulse durations; a second waveform frequency that is non-zero; causing, a first alternating current having one or more first pulses to flow for a first length of time through a coil according to the first waveform frequency; causing, a second alternating current having one or more second pulses to flow through the coil for a second length of time according to the second waveform frequency lower than the first waveform frequency. The method includes repeating the causing of the first and second alternating currents for a plurality of iterations to provide a continuously pulsed time-varying magnetic field that alternates between the first and the second waveform frequencies to generate a treatment session.

14 Claims, 19 Drawing Sheets

(56) References Cited

U.S. PATENT DOCUMENTS

| 11,590,356 | B2 | 2/2023 | Schwarz et al. |
| 11,691,024 | B2 | 7/2023 | Schwarz et al. |
| 11,794,029 | B2 | 10/2023 | Schwarz et al. |
| 2018/0001107 | A1 | 1/2018 | Schwarz et al. |
| 2019/0201706 | A1 | 7/2019 | Schwarz et al. |

ENERGY DELIVERY VALUES 290

Satisfy at least one of (for high frequency):
1. Tissue-Independent Integrated Electric Charge / Electrical Conductivity >= 0.115 millivolt second meters (mV * s * m)
2. Maximum Magnetic Flux Density = 1.3 to 1.4 teslas (T)
3. Maximum Current Density norm >= 40 amps / square meter (A/m$^2$)
4. Induced Current Peak-to-peak >= 70 milliamps (mA)

PARAMETER RANGE 292

Satisfy each of:
1. Pulse amplitude = Approx. 2000 A
2. Pulse duration / width = Approx. 300-450 microseconds (µS) (2.2 to 3.3 KHz)
3. First (High Frequency) Waveform frequency = Approx. 10-50 pulses per second (pps, or Hz for AC waveform)
Resulting in a pulse charge (Integrated Electric Charge) >= 6.4 µC 4. Second (Low Frequency) Waveform frequency = Approx. 4-6 pulses per second (pps / Hz)
5. Duration of each High Frequency portion is between 2-12 seconds. Duration of each Low Frequency portion is between 2-12 seconds (for recovery portion of the treatment session) and between 30-80 seconds (for recovery session).
6. Ratio of a length of time of the high frequency portion of to a length of time of the low frequency portion not to exceed 6:4 or fall below 4:6

PARAMETER SET 294A (HIGH FREQUENCY)

Set pulse parameter values to:
1. Pulse amplitude = 2000 A
2. Pulse duration = 360 µS (Pulse Frequency = approx. 2.8KHz)
3. Waveform frequency = 10-50 Hz
To result in a pulse charge of approx. 8 µC during high intensity stimulation
4. Length of the time of the high frequency portion = 2-12 seconds

PARAMETER SET 294B (LOW FREQUENCY)

Set pulse parameter values to:
1. Pulse amplitude = 2000 A
2. Pulse duration = 360 µS (Pulse frequency = approx. 2.8KHz)
3. Waveform frequency = 2-10 Hz
To provide a low intensity recovery period with stimulation
4. Length of time of the low frequency portion = 2-12 seconds or 30-80 seconds.

FIG. 2A

| Phase # | Freq (Hz) | Time On (s) | Time Recovery @4Hz (s) | Strength (%) | Repetitions | Total On (sec) | Total Recovery (sec) | Contraction Pulses | Recovery Pulses (4Hz) | Total Pulses |
|---|---|---|---|---|---|---|---|---|---|---|
| 1 | 5 | 10 | 0 | 75% | 12 | 120 | 0 | 600 | 0 | 600 |
| 2 | 25 | 5 | 6 | 100% | 32 | 160 | 192 | 4000 | 768 | 4768 |
| 3 | 5 | 5 | 0 | 75% | 9 | 45 | 0 | 225 | 0 | 225 |
| 4 | 25 | 5 | 6 | 100% | 31 | 155 | 186 | 3875 | 744 | 4619 |
| 5 | 5 | 5 | 0 | 75% | 10 | 50 | 0 | 250 | 0 | 250 |
| 6 | 40 | 5 | 6 | 80% | 31 | 155 | 186 | 6200 | 744 | 6944 |
| 7 | 5 | 5 | 0 | 75% | 14 | 70 | 0 | 350 | 0 | 350 |
| 8 | 40 | 5 | 6 | 80% | 29 | 145 | 174 | 5800 | 696 | 6496 |
| 9 | 5 | 10 | 0 | 75% | 8 | 80 | 0 | 400 | 0 | 400 |
| 10 | 5 | 10 | 0 | 60% | 8 | 80 | 0 | 400 | 0 | 400 |
| 11 | 5 | 2 | 0 | 60% | 1 | 2 | 0 | 10 | 0 | 10 |

Sequence Totals: 1062 738 22110 2952 25062
Minutes on/recovery: 17.7 12.3
Total Sequence Time (min): 30.00

FIG. 2I

| Phase # | Freq (Hz) | Time on (s) | Recovery (s) (4Hz) | Strength | Repetitions | Total On (sec) | Total Recovery (sec) | On Pulses | Recovery Pulses | Total Pulses |
|---|---|---|---|---|---|---|---|---|---|---|
| 1 | 5 | 10 | 0 | 75% | 12 | 120 | 0 | 600 | 0 | 600 |
| 2 | 18 | 5 | 6 | 100% | 30 | 150 | 180 | 2700 | 720 | 3420 |
| 3 | 5 | 5 | 0 | 75% | 13 | 65 | 0 | 325 | 0 | 325 |
| 4 | 18 | 5 | 6 | 100% | 30 | 150 | 180 | 2700 | 720 | 3420 |
| 5 | 5 | 5 | 0 | 75% | 13 | 65 | 0 | 325 | 0 | 325 |
| 6 | 35 | 5 | 6 | 80% | 30 | 150 | 180 | 5250 | 720 | 5970 |
| 7 | 5 | 5 | 0 | 75% | 13 | 65 | 0 | 325 | 0 | 325 |
| 8 | 35 | 5 | 6 | 80% | 30 | 150 | 180 | 5250 | 720 | 5970 |
| 9 | 5 | 10 | 0 | 75% | 12 | 120 | 0 | 600 | 0 | 600 |
| 10 | 5 | 45 | 0 | 60% | 1 | 45 | 0 | 225 | 0 | 225 |
| | | | | Sequence Totals: | | 1080 | 720 | 18300 | 2880 | 21180 |
| | | | | Minutes on/recovery: | | 18 | 12 | | | |
| | | | | Total Sequence Time (min): | | | | | | 30.0 |

FIG. 2J

| Phase # | Freq (Hz) | Time on (s) | Recovery (s) @4 Hz | Strength (%) | Repetitions | Total On (sec) | Total Recovery (sec) | On Pulses | Recovery Pulses | Total Pulses |
|---|---|---|---|---|---|---|---|---|---|---|
| 1 | 5 | 10 | 0 | 75% | 9 | 90 | 0 | 450 | 0 | 450 |
| 2 | 20 | 5 | 6 | 100% | 23 | 115 | 138 | 2300 | 552 | 2852 |
| 3 | 5 | 5 | 0 | 75% | 10 | 50 | 0 | 250 | 0 | 250 |
| 4 | 20 | 5 | 6 | 100% | 23 | 115 | 138 | 2300 | 552 | 2852 |
| 5 | 5 | 5 | 0 | 75% | 11 | 55 | 0 | 275 | 0 | 275 |
| 6 | 30 | 6 | 6 | 80% | 14 | 84 | 84 | 2520 | 336 | 2856 |
| 7 | 5 | 5 | 0 | 75% | 12 | 60 | 0 | 300 | 0 | 300 |
| 8 | 30 | 6 | 6 | 80% | 14 | 84 | 84 | 2520 | 336 | 2856 |
| 9 | 5 | 10 | 0 | 75% | 9 | 90 | 0 | 450 | 0 | 450 |
| 10 | 5 | 13 | 0 | 60% | 1 | 13 | 0 | 65 | 0 | 65 |
| | | | | Sequence Totals: | | 756 | 444 | 11430 | 1776 | 13206 |
| | | | | Minutes on/Recovery: | | 12.6 | 7.4 | | | |
| | | | | Total Sequence Time (min): | | | | | | 20.0 |

FIG. 2K

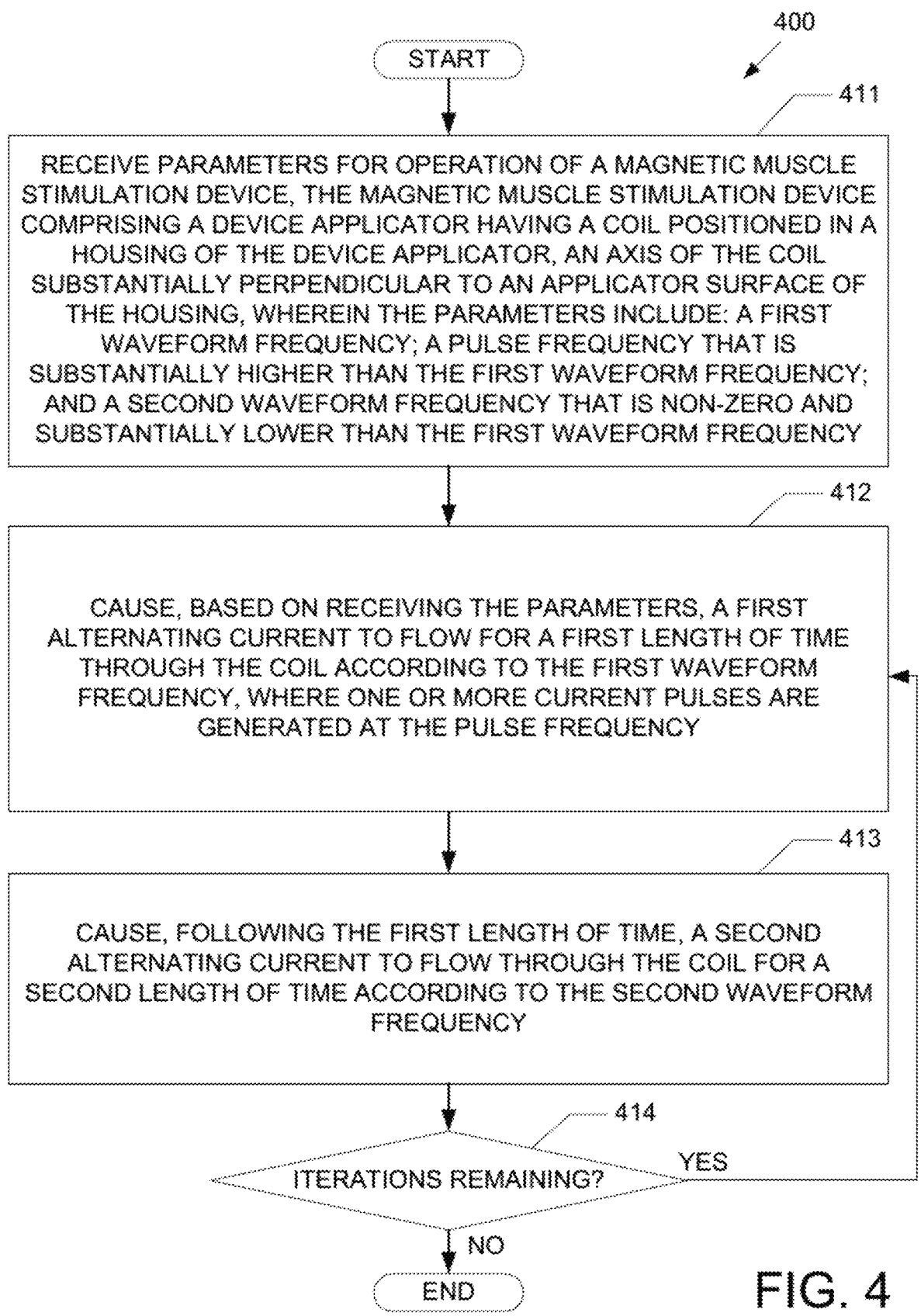

ALTERNATING HIGH FREQUENCY AND LOW FREQUENCY DUTY CYCLES FOR MUSCLE STIMULATION

CROSS-REFERENCE TO RELATED APPLICATIONS

This application claims the benefit under 35 U.S.C. 119(e) to U.S. Provisional Application Ser. No. 62/938,222, filed on Nov. 20, 2019, entitled "Alternating High and Low Duty Cycles for Effective Muscle Stimulation," which is incorporated herein by reference in its entirety.

TECHNICAL FIELD

The present disclosure generally relates to muscle stimulation, and more specifically relates to methods and systems for using pulsed electromagnetic energy with alternating high frequency and low frequency duty cycles to provide effective muscle stimulation for toning, strengthening, and firming of muscle tissues.

BACKGROUND

Muscle stimulation technologies such as electrical muscle stimulation (EMS) can be helpful for applications such as workout recovery and enhancement, physical therapy, and muscle strengthening and toning. EMS devices often require a large number of electrodes to be attached to the skin of the user, which may present a high barrier for regular use. Electrical current is emitted by positive electrodes, passes through skin and other tissue, including muscle, then is returned to the EMS device via negative electrodes. Providing sufficient levels of electrical current with EMS devices to stimulate the muscle tissues often causes nerve endings to be unduly stimulated as well, causing unwanted side effects and discomfort to the user, and limiting the amount of current which can be used.

Other forms of muscle stimulation are also available, such as magnetic muscle stimulation (MMS). These technologies seek to stimulate muscle tissues through electromagnetic fields, avoiding cumbersome skin electrodes and unwanted nerve stimulation which results by bidirectionally passing current through the skin as a means of getting the current to the muscle. However, existing devices are still developing technology and may not currently meet user expectations in regards to, for example, muscle strength, muscle toning, muscle firming, user comfort, safety, the number of therapy sessions required and the length of the treatment period before readily perceivable and tangible results can be realized. Accordingly, there is a need for improved muscle stimulation methods and systems that can deliver highly effective muscle tissue stimulation to remedy these deficiencies.

SUMMARY

According to various implementations, a method for providing continuously pulsed electromagnetic energy with alternating low frequency and high frequency duty cycles to deliver effective amounts of electromagnetic charge to muscle tissues is provided. The method may include receiving parameters for operation of a device applicator of a magnetic muscle stimulation device. The parameters may include a first waveform frequency, a pulse duration of between 300-450 microseconds, and a second waveform frequency that is non-zero and substantially lower than the first waveform frequency. The method may include causing, based on receiving the parameters, a first alternating current having one or more first pulses to flow for a first length of time through the coil according to the first waveform frequency. The method may include causing, following the first length of time, a second alternating current having one or more second pulses to flow through the coil for a second length of time according to the second waveform frequency. The method may include repeating the causing of the first and second alternating currents for a plurality of iterations to provide a continuously pulsed time-varying magnetic field that alternates between the first and the second waveform frequencies.

Various aspects of the present technology are recited below.

In one aspect of the present technology, a method for strengthening, toning, and firming muscle tissues is provided. The method may include receiving parameters for operation of a magnetic muscle stimulation device, the magnetic muscle stimulation device comprising a device applicator having a coil positioned in a housing of the device applicator, an axis of the coil substantially perpendicular to an applicator surface of the housing, wherein the parameters include: a first waveform frequency of 10-50 Hz, a second waveform frequency of 2-10 Hz; a third waveform frequency of between 2-10 Hz; a pulse duration of 300-450 microseconds; and an individual pulse frequency of 2.2-3.3 kHz, the individual pulse frequency being substantially higher than the first waveform frequency. The method may also include causing, based on receiving the parameters, a first alternating current having one or more first pulses to flow for a first length of time through the coil according the first waveform frequency, each of the one or more first pulses has the pulse duration of 300-450 microseconds and the individual pulse frequency of 2.2-3.3 kHz. The method includes causing, following the first length of time, a second alternating current having one or more second pulses to flow through the coil for a second length of time according to the second waveform frequency that is lower than the first waveform frequency. Each of the one or more second pulses has the pulse duration of 300-450 microseconds and the individual pulse frequency of 2.2-3.3 kHz. The method includes repeating the causing of the first and second alternating currents for a plurality of iterations to provide a continuously pulsed time-varying magnetic field that alternates between the first and the second waveform frequencies. The first length of time is 2-12 seconds, and the second length of time is 2-12 seconds, and the plurality of iterations is 10-140 iterations, thereby generating a treatment session having a length of 100-1000 seconds. The method includes causing, based on receiving the parameters, a third alternating current having one or more third pulses to flow through the coil for a third length of time according to the third waveform frequency, thereby generating a recovery session. Each of the one or more third pulses has the pulse duration of 300-450 microseconds and the individual pulse frequency of 2.2-3.3 kHz, the third length of time is 30-80 seconds. The method includes generating a plurality of the treatment sessions, a pair of adjacent treatment sessions being separated by the recovery session. The first, second, and third waveform frequencies provide a continuously pulsed time-varying magnetic field that alternates between the first, second and third waveform frequencies. A magnetic flux density generated by the magnetic muscle stimulation device is between 1.2-2.0 tesla (T), an inductance of the coil is between 30-50 micro Henry (mH), the coil has an inner diameter between 0-50 mm, and an outer diameter of between 50-150 mm.

In a further aspect of the present technology, the method further includes causing, based on receiving the parameters, a fourth alternating current having one or more fourth pulses to flow through the coil for a fourth length of time according to a fourth waveform frequency of between 2-10 Hz, thereby generating a warmup session. The method includes causing, based on receiving the parameters, a fifth alternating current having one or more fifth pulses to flow through the coil for a fifth length of time according to a fifth waveform frequency of between 2-10 Hz, generating a warm up session prior to the treatment and recovery sessions, and a cool down session following the treatment and recovery sessions. The first, second, third, fourth, and fifth waveform frequencies provide a continuously pulsed time-varying magnetic field that alternates between the first, second, third, fourth, and fifth waveform frequencies.

In a further aspect of the present technology, the second waveform frequency is 33% (⅓) or less than the first waveform frequency.

In a further aspect of the present technology, the second waveform frequency is 25% (¼) or less than the first waveform frequency.

In a further aspect of the present technology, the second waveform frequency is 20% (⅕) or less than the first waveform frequency.

In a further aspect of the present technology, the second waveform frequency is approximately 5 Hz or less.

In a further aspect of the present technology, a ratio of the first length of time to the second length of time does not exceed 6:4 or fall below 4:6.

In a further aspect of the present technology, the first or second length of time is approximately 6 seconds.

In a further aspect of the present technology, the first waveform frequency is approximately 18 to 40 hertz (Hz).

In a further aspect of the present technology, at least one of the first or second waveforms has a sinusoidal or biphasic waveform.

In a further aspect of the present technology, the plurality of iterations include no idle time between the iterations.

In another aspect of the present technology, a magnetic muscle stimulation device for strengthening, toning, and firming muscle tissues is provided, the magnetic muscle stimulation device including a device applicator comprising a housing having a substantially flat applicator surface, and a coil positioned in the housing with an axis of the coil substantially perpendicular to the applicator surface. The magnetic muscle stimulation device may also include a processor configured to receive parameters including: a first waveform frequency of 10-50 Hz, a second waveform frequency of 2-10 Hz, a third waveform frequency of between 2-10 Hz, a pulse duration of 300-450 microseconds, and an individual pulse frequency of 2.2-3.3 kHz, the individual pulse frequency being substantially higher than the first waveform frequency. The processor may be further configured to cause, based on receiving the parameters, a first alternating current having one or more first pulses durations to flow for a first length of time through the coil according to the first waveform frequency. Each of the one or more first pulses has the pulse duration of 300-450 microseconds and the individual pulse frequency of 2.2-3.3 kHz. The processor may be further configured to cause, following the first length of time, a second alternating current having one or more second pulses to flow through the coil for a second length of time according to the second waveform frequency. Each of the one or more second pulses has the pulse duration of 300-450 microseconds and the individual pulse frequency of 2.2-3.3 kHz The processor may be further configured to repeat the causing of the first and second alternating currents for a plurality of iterations to provide a continuously pulsed time-varying magnetic field that alternates between the first and the second waveform frequencies. The first length of time is 2-12 seconds, and the second length of time is 2-12 seconds, and the plurality of iterations is 10-140 iterations, thereby generating a treatment session, a length of the treatment session is 100-1000 seconds. The processor may be further configured to cause based on receiving the parameters, a third alternating current having one or more third pulses to flow through the coil for a third length of time according to the third waveform frequency, thereby generating a recovery session. Each of the one or more third pulses has the pulse duration of 300-450 microseconds and the individual pulse frequency of 2.2-3.3 kHz, and the third length of time is 30-80 seconds; and generate a plurality of the treatment sessions, a pair of adjacent treatment sessions being separated by the recovery session. The first, second, and third waveform frequencies provide a continuously pulsed time-varying magnetic field that alternates between the first, second and third waveform frequencies, a magnetic flux density generated by the magnetic muscle stimulation device is between 1.2-2.0 tesla (T), an inductance of the coil is between 30-50 micro Henry (mH), and the coil has an inner diameter between 0-50 mm, and an outer diameter of between 50-150 mm.

In further aspects of the present technology, the magnetic muscle stimulation device may be configured according to the various aspects described above.

In yet another aspect of the present technology, a non-transitory computer-readable medium is provided that comprises a plurality of instructions that, when read by a computing system, causes the computing system to perform the methods described in the various aspects above.

In still yet another aspect of the present technology, an alternative method is provided for strengthening, toning, and firming muscle tissues. The alternative method may include providing a magnetic muscle stimulation device, the magnetic muscle stimulation device comprising an applicator having a coil positioned in a housing of the applicator, an axis of the coil substantially perpendicular to an applicator surface of the housing. The alternative method may also include causing a first alternating current to flow through the coil for a first length of time according to a first waveform frequency, wherein each period comprises a first period of time in which one or more current pulses are generated, the one or more current pulses having one or more pulse durations of between 300-450 microseconds, each corresponding to a pulse frequency between 2.2-3.3 kHz, followed by a second alternating current to flow through the coil for a second length of time according to a second waveform frequency that is non-zero and substantially lower than the first waveform frequency. The alternative method may also include repeating the causing of the first and second alternating currents for a plurality of iterations to provide a continuously pulsed time-varying magnetic field that alternates between the first and the second waveform frequencies, wherein the first waveform frequency is between 10-50 Hz, the second waveform frequency is between 2-10 Hz, the first length of time is between 2-12 seconds, and the second length of time is between 2-12 seconds, and the plurality of iterations is between 10-140 iterations, thereby creating a treatment session, a length of the treatment session is 100-1000 seconds, a magnetic flux density generated by the magnetic muscle stimulation device is between 1.2-2.0 tesla (T), an inductance of the coil is between 30-50 micro Henry (mH), and the coil has an inner diameter between 0-50 mm, and an outer diameter of between 50-150 mm.

In further aspects of the present technology, the alternative method may be modified according to the various aspects described above.

In another aspect of the present technology, a method for strengthening, toning, and firming muscle tissues, the method includes receiving parameters for operation of a magnetic muscle stimulation device, the magnetic muscle stimulation device comprising a device applicator having a coil positioned in a housing of the device applicator, an axis of the coil substantially perpendicular to an applicator surface of the housing. The parameters include: a first waveform frequency; a pulse frequency that is substantially higher than the first waveform frequency; and a second waveform frequency that is non-zero and substantially lower than the first waveform frequency; causing, based on receiving the parameters, a first alternating current having the pulse frequency to flow for a first length of time through the coil according to the first waveform frequency. The method includes causing, following the first length of time, a second alternating current having the pulse frequency to flow through the coil for a second length of time according to the second waveform frequency that is lower than the first waveform frequency. The method includes repeating the causing of the first and second alternating currents for a plurality of iterations to provide a continuously pulsed time-varying magnetic field that alternates between the first and the second waveform frequencies.

In a further aspect of the present technology, the first waveform frequency is between 10-50 Hz, the second waveform frequency is between 2-10 Hz, the first length of time is between 3-15 seconds, the second length of time is between 3-150 seconds, and the plurality of iterations is between 2-40 iterations.

In a further aspect of the present technology, the second length of time is between 3-15 seconds, and the plurality of iterations is between 8-40, the continuously pulsed time-varying magnetic field defining a treatment session.

In a further aspect of the present technology, the second length of time is between 30-80 seconds, and the plurality of iterations is between 2-8, the continuously pulsed time-varying magnetic field defining at least part of a treatment session and a recovery session between treatment sessions.

In a further aspect of the present technology, the method further includes a plurality of treatment sessions, each pair of adjacent treatment sessions being separated by a recovery session, and further comprising a third waveform frequency, and further causing a third alternating current having the one or more pulse durations to flow through the coil for a third length of time which is between 30-80 seconds according to the third waveform frequency, the third waveform frequency being between 2-10 Hz, the first, second, and third waveform frequencies providing a continuously pulsed time-varying magnetic field that alternates between the first, second and third waveform frequencies so as to create treatment sessions separated by recovery sessions.

In a further aspect of the present technology, the method further includes a warm up session prior to the treatment and recovery sessions, and a cool down session following the treatment and recovery sessions, the warm up session including a fourth waveform frequency that is between 2-10 Hz, the cool down session including a fifth waveform frequency that is between 2-10 Hz, and further causing a fourth alternating current having the one or more pulse durations to flow through the coil for a fourth length of time according to the fourth waveform frequency, and causing a fifth alternating current having the one or more pulse durations to flow through the coil for a fifth length of time according to the fifth waveform frequency, to provide a continuously pulsed time-varying magnetic field that alternates between the first, second, third, fourth, and fifth waveform frequencies.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

BRIEF DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIG. 2A depicts example optimized parameters, including high frequency and low frequency parameters for use with the system of FIG. 1A, according to various aspects of the subject technology.

FIG. 2I depicts an example treatment sequence for the abdomen, according to various aspects of the subject technology.

FIG. 2J depicts an example treatment sequence for the buttocks, according to various aspects of the subject technology.

FIG. 2K depicts an example treatment sequence for the thighs, according to various aspects of the subject technology.

FIG. 4 depicts an example process for using alternating high frequency portions and low frequency portions of the treatment waveforms to deliver effective amounts of electromagnetic charge to muscle tissues, according to various aspects of the subject technology.

DETAILED DESCRIPTION

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

The subject technology provides a magnetic muscle stimulation device for delivering continuously pulsed electromagnetic current and charge to muscles for strengthening, toning, and firming muscle tissues. In particular, a tissue-independent integrated electrical charge/tissue electrical conductivity (also referred to as "delivery value") is defined to express the total electrical charge delivered to muscle tissues. Since the delivery value is tissue-independent, it can be used to define effective charge delivery regardless of patient variations in individual muscle response. Further, this delivery value can be adjusted according to application and use-case requirements for electrical consumption, thermal dissipation, and device form factor. Parameter ranges can be defined based on satisfying a target delivery value and other parameters, and a particular parameter set falling within the parameter ranges can be determined for driving one or more coils of an electromagnetic device applicator to deliver the target delivery value to muscle tissues of a patient.

Figure 1A:
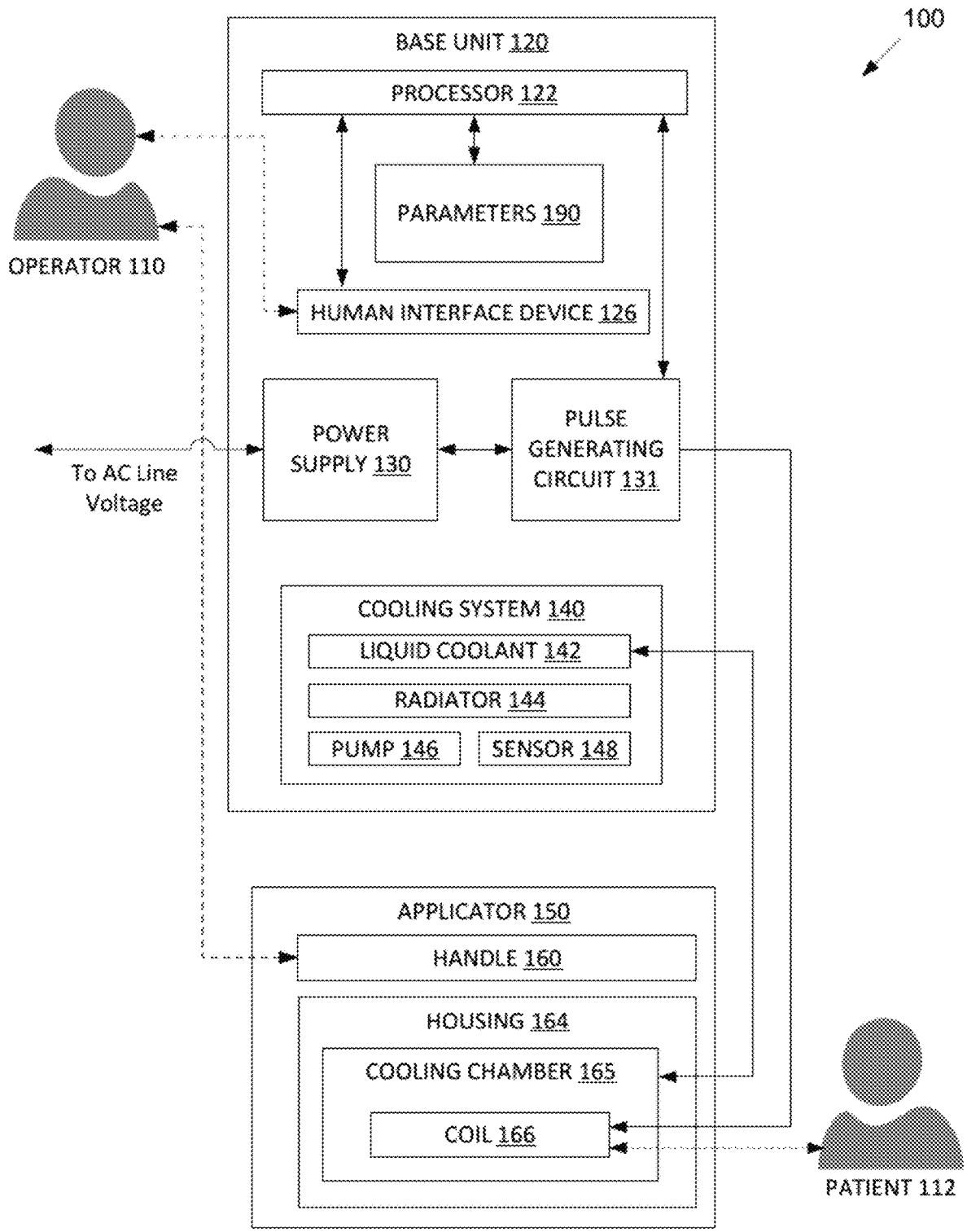
FIG. 1A depicts an example system for using optimized high frequency and low frequency duty cycle parameters to deliver effective amounts of electromagnetic charge to muscle tissues, according to various aspects of the subject technology.

FIG. 1A depicts an example system 100 for using parameters 190, which may include high frequency and low frequency parameters for delivering effective amounts of continuously pulsed electromagnetic charge to muscle tissues of patient 112, according to various aspects of the subject technology. Base unit 120 includes processor 122, human interface device 126, power supply 130, pulse generating circuit 131, cooling system 140, and parameters 190. Cooling system 140 includes liquid coolant 142, radiator 144, pump 146, and sensor 148. Applicator 150 includes handle 160 and housing 164. A cover may optionally attach to the outside of housing 164 and/or handle 160.

As shown in FIG. 1A, operator 110 may use human interface device 126 to control base unit 120. Operator 110 may correspond to a healthcare professional, such as a doctor or nurse, that is trained in the usage of system 100. Human interface device 126 includes an input and/or an output device, and may be implemented as, for example, a touchscreen panel, a keypad and a display, or a similar interface device. In one embodiment, operator 110 may use human interface device 126 to adjust parameters 190, or to select or define a parameter set that satisfies parameters 190. In some implementations, parameters 190 may be predetermined at manufacture time and may not be changed by operator 110. In this case, parameter sets may also be predefined, or operator 110 may select from one or more predetermined parameter ranges or parameter sets, as shown in greater detail in FIG. 2A.

Base unit 120 may include several other components, as shown in system 100. Base unit 120 may include processor 122, which may correspond to any type of general or specialized processor, controller, integrated circuit, application specific integrated circuit (ASIC), field programmable gate array (FPGA), system-on-chip, or similar device, and may include hardcoded circuit elements, firmware, software, or any combination thereof.

Base unit 120 may include power supply 130, which may be any type of power supply, such as a switching power supply, and may be connected to AC line voltage mains, for example 100V AC to 230V AC. Power supply 130 may provide power to pulse generating circuit 131, which may in turn excite coil 166 based on parameters 190. Power supply 130 may be a separate and independent power supply from a general power supply (not shown) that supplies power to other components of base unit 120, such as processor 122, human interface device 126, and cooling system 140. In some implementations, one or more batteries or other alternative power sources may be provided to provide a graceful shutdown or to continue operation in the event power supply 130 or the general power supply fails.

Base unit 120 may include cooling system 140, which is preferably a high performance cooling system such as a liquid cooling system. Air cooling may also be used but may be insufficient to meet the operating demands of parameters 190 when optimized for high performance muscle stimulation. As shown in system 100, cooling system 140 is a liquid cooling system that includes liquid coolant 142, radiator 144, pump 146 and sensor 148. Pump 146 may be used to circulate liquid coolant 142, which may be thermally coupled to coil 166 and other heat generating components of system 100. Radiator 144 may be used to regulate the temperature of liquid coolant 142 to keep coil 166 and housing 164 in a safe operating temperature range. For example, one or more fans may be coupled to radiator 144 to disperse heat from liquid coolant 142 into the atmosphere. Alternative implementations may directly couple cooling system 140 to a central heating ventilation and air conditioning (HVAC) system. Sensor 148 may detect the temperature of liquid coolant to allow fans on radiator 144 to be ramped up or down in speed and to provide processor 122 with temperature monitoring.

Figure 1B:
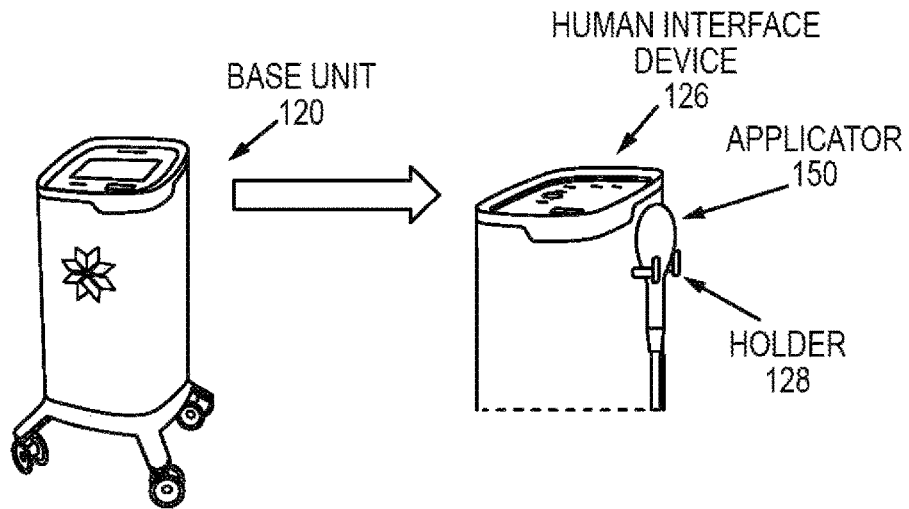
FIG. 1B depicts perspective views of an example base unit for use with the system of FIG. 1A, according to various aspects of the subject technology.

To begin a therapy session, operator 110 may use handle 160 of applicator 150 to position applicator 150 above and substantially parallel to a skin layer of the patient, such that coil 166 stimulates the muscle tissues of patient 112 for toning, strengthening, and firming of the muscle tissues. In this regard, processor 122 may direct pulse generating circuit 131 to generate a waveform to flow into coil 166 of applicator 150 (FIG. 1D). To excite coil 166 according to parameters 190, processor 122 may direct pulse generating circuit 131 to generate an alternating current (AC) waveform having a specific parameter set of parameter values, as described in further detail in FIG. 2A. While coil 166 is shown as a single coil, it should be understood that coil 166 may comprise multiple adjacent coils, for example, operating in parallel.

Pulse generating circuit 131 is operably connected to processor 122 and may contain one or more capacitors and one or more switching elements that operate to generate a current through coil 166. Pulse generating circuit 131 may define, together with coil 166, a LC resonant circuit. The switching frequency of the switching elements may be controlled by processor 122 to charge and discharge capacitors in a coordinated manner according to parameters 190, to generate an alternating current through coil 166. The geometry of coil 166 and the waveform of the current flowing through coil 166 cause the coil to generate a time-varying magnetic field of a desired field strength. The rate of change of the magnetic field induces a corresponding electric current within neuromuscular tissue at a given distance from the coil. As will be described further, processor 122 is configured to, when configured with a set of predefined parameters, drive pulse generating circuit 131 to cause an alternating current to flow through the coil to generate a time-varying magnetic field sufficient to generate an integrated electric charge divided by electrical conductivity, per pulse, equal to or greater than 0.115 millivolt second meters (mV*s*m) in muscle tissue under a skin layer of a patient. It has been found that integrated electric charge/electrical conductivity less than 0.115 mV*s*m under treat patients and create unsatisfactory results. Optimally, the integrated electric charge/electrical conductivity can exceed any of 0.12, 0.13, 0.14, 0.15, 0.16, 0.17, 0.18, 0.19, 0.20, 0.22, 0.25 mV*s*m, and be between 0.12-0.75 mV*s*m.

As the charge is increased, patient discomfort can increase, so the upper value can be adjusted based on patient feedback either during clinical trials or during patient treatment. According to various implementations, this desired integrated electric charge/electrical conductivity is generated when the applicator surface is positioned between, for example, 0 mm and 10 mm above and substantially parallel to the skin layer of the patient (see FIG. 3A).

While pulse generating circuit 131 is shown in FIG. 1A as part of base unit 120, pulse generating circuit 131 may be incorporated in applicator 150, for example, in close proximity to coil 166, and driven by signals generated by processor 122 from base unit 120. Pulse generating circuit 131 may include one or more capacitors with a rated voltage of approximately 1300-1700 volts and a rated capacitance of approximately 70-110 microfarads, e.g., 90 microfarads in one example. An inductance of the coil 166 may be between 30-50 micro Henry (mH), for example, between 36-39 mH. In some implementations, pulse generating circuit 131 may be specified to recapture at least 75% of the electrical energy from the capacitors. The charging and discharging of the capacitors generates a waveform through the coil that approximates a desired arbitrary function in accordance with parameters 190. Other circuit elements may also be included to shape the waveform, such as polarity switchers and variable resistors. The particular waveform generated by way of a given set of parameters is used to energize coil 166 in a corresponding manner, which in turn generates a corresponding magnetic field that induces an effective amount of electrical current in the muscle tissues of patient 112.

Applicator 150 includes a housing 164 and a handle 160 for holding by an operator, such as operator 110. Housing 164 contains coil 166 in a fixed position with an axis of coil 166 substantially perpendicular to an applicator surface of the housing and may be formed from a molded plastic or other material. Housing 164 may preferably be a material with low thermal conductivity to prevent skin burns and improve comfort. Coil 166 may be a high performance, tightly wound metallic coil, such as a copper coil. In some implementations, the outer diameter of coil 166 may be less than 60, 80, 100, 120, 140, 160, 180, 200 mm, for example, the outer diameter of the coil 166 may be approximately 130 mm, the inner diameter of coil 166 may be zero or less than 5, 10, 20, 30, 40, 50 mm, for example being between 0-50 mm, for example, the inner diameter of the coil 166 may be approximately 30 mm, and the winding cross sections of coil 166 may be approximately 7-8 mm by 1.8 mm. The windings of coil 166 may be formed from a single or multistranded wire. In some implementations, approximately 24 windings may be provided in coil 166. The wire conductor may be coated with a non-conductive material. In some implementations, the windings of coil 166 may be litz-wire, in which each wire strand of a multistranded wire is separately insulated. According to various implementations, coil 166 may be configured as a planar coil. In some implementations, coil 166 may be a toroidal coil. According to various implementations, the (mean) azimuthal direction of current flow through the coil is substantially parallel to the applicator surface in contact or directly above the skin of the patient, with the axis of the coil substantially perpendicular to the applicator surface, such that the magnetic field flows through the skin into corresponding neuromuscular tissue of the patient. As depicted in FIG. 1A, coil 166 may be thermally coupled to cooling chamber 165, which may at least partially surround coil 166 and be at least partially filled with liquid coolant 142.

Since applicator 150 operates on electromagnetic principles, there is no need for electrode electrical contact with patient 112. In some implementations, an optional cover may be provided, which may serve as a removably attachable barrier to housing 164 to prevent contact between the applicator and the skin of patient 112 or clothing, and may further facilitate surface cooling, as coil 166 may elevate the temperature of housing 164. The presence of the cover provides a physical barrier that prevents contact of the applicator with the patient's skin or clothing. The barrier cover may be disposable and fabricated using materials with low thermal conductivity to increase comfort for patient 112. Alternatively or additionally, housing 164 may be shaped to help prevent contact (e.g., with the patient's skin or clothing), as described below in conjunction with FIG. 1C.

With a block diagram overview of system 100 now in place, it may be helpful to observe various perspective views of the components of system 100. FIG. 1B depicts perspective views of base unit 120 for use with system 100 of FIG. 1A, according to various aspects of the subject technology. As shown in FIG. 1B, base unit 120 may be coupled to casters for mobility. Human interface device 126 may be provided as a touchscreen display on top of base unit 120. Applicator 150 may be tethered to base unit 120 via a cable that provides current from power supply 130 and liquid coolant 142 from cooling system 140. As shown in FIG. 1B, applicator 150 may be conveniently docked to a side of base unit 120 via holder 128. While only a single applicator 150 is shown in the perspective views of FIG. 1B, some implementations may include multiple applicators, which may be hardwired to or detachable from base unit 120.

Figure 1C:
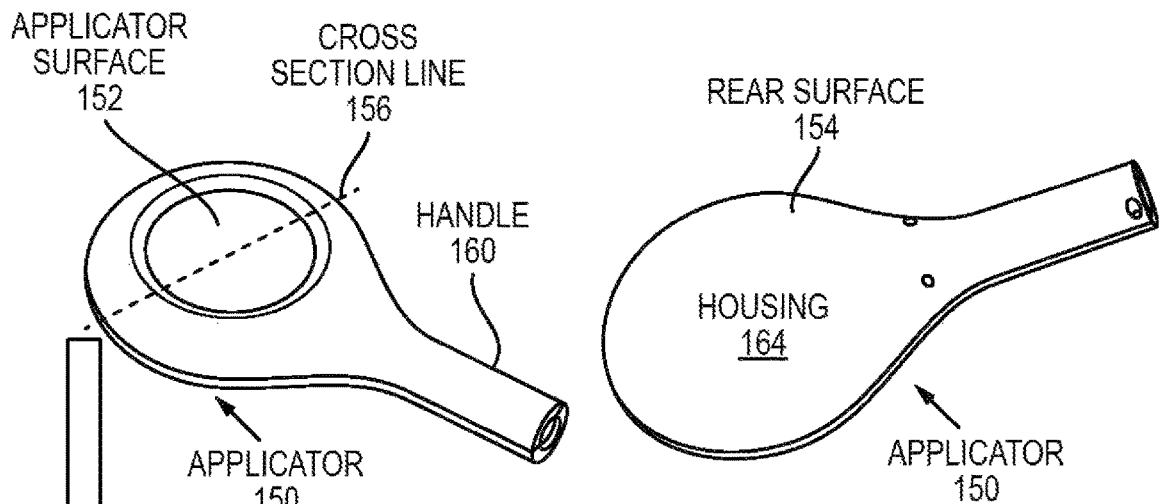
FIG. 1C depicts perspective views of an example electromagnetic applicator for use with the system of FIG. 1A, according to various aspects of the subject technology.
Figure 1D:
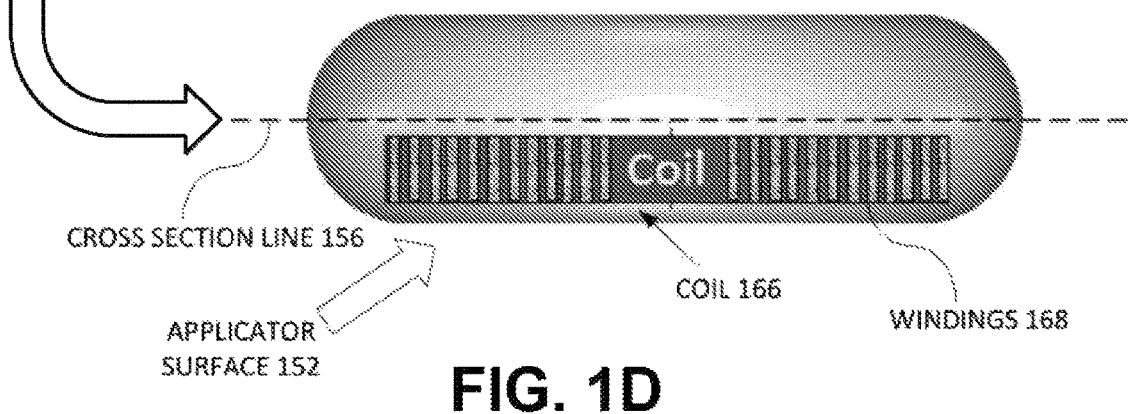
FIG. 1D depicts a cross-sectional view of the example electromagnetic applicator of FIG. 1C, according to various aspects of the subject technology.

FIG. 1C depicts perspective views of applicator 150 for use with system 100 of FIG. 1A, according to various aspects of the subject technology. As shown in FIG. 1C, housing 164 of applicator 150 may be a two-piece molded assembly that is fastened together, e.g. by screws, and includes applicator surface 152, rear surface 154, and handle 160. Some implementations may use different materials, assembly techniques, and fasteners. Applicator surface 152 may be shaped as a substantially flat, circular surface to conform to the shape of coil 166. Applicator surface 152 may also be surrounded by raised edges of housing 164 to assist in preventing applicator surface 152 from contacting the skin of a patient. Alternatively or additionally, cover 164 (not shown) may be wrapped around housing 164.

FIG. 1D depicts a cross-sectional view of applicator 150 of FIG. 1C, according to various aspects of the subject technology. As shown in FIG. 1C and FIG. 1D, cross section line 156 cuts across the center of applicator 150 between applicator surface 152 and rear surface 154. Coil 166 includes windings 168 and is positioned close to applicator surface 152. While not specifically shown in FIG. 1D, applicator 150 may also include thermal interface materials to thermally couple coil 166 to pipes containing liquid coolant 142. For example, referring to FIG. 1A, applicator 150 may be provided with cooling chamber 165 that at least partially surrounds coil 166, wherein the cooling chamber is at least partially filled with liquid coolant 142. In this manner, the applicator surface 152 may be kept below an operating temperature of coil 166 when applicator 150 is in operation, or receiving current from power supply 130.

FIG. 2A depicts example energy delivery values 290 of the system 100 of FIG. 1A, according to various aspects of the subject technology. FIG. 2A also depicts parameter range 292 and parameter set 294A and 294B, also referred to as "operating parameters" that may be set to achieve one or more of energy delivery values 290. With respect to FIG. 2A, energy delivery values 290, parameter range 292, and/or parameter set 294A and parameter set 294B may correspond to parameters 190 from FIG. 1A.

Delivery values 290 have been found to bring about the optimal amount of neuro-stimulation in nerve fibers and neuromuscular tissue of a patient. It should be understood that example energy delivery values 290 can be programmed directly, or generated by means of programing system 100 with a parameter set selected from operating parameters 292, 294A, 294B. Delivery values 290, and/or operating parameters 292, 294A, 294B, may be further adjusted according to individual use cases to balance, for example, electrical charge delivery to muscles, power consumption, thermal dissipation, and device form factor. When programmed directly (e.g., by way of user interface 126), system 100 may automatically calculate a parameter set 294A, 294B sufficient to achieve the desired delivery values 290.

A first value of delivery values 290, or tissue-independent integrated electrical charge/electrical conductivity ("delivery value") is defined to be at least 0.115 millivolt second meters (mV*s*m). In some implementations, the delivery value may be defined to exceed any of 0.12, 0.13, 0.14, 0.15, 0.16, 0.17, 0.18, 0.19, 0.20, 0.22, 0.25 mV*s*m, and be between 0.12-0.75 mV*s*m, and in one preferred embodiment exceeding 0.14 mV*s*m. In some implementations, the delivery value may be defined to be between 0.15 mV*s*m and 0.75 mV*s*m. These delivery values may be further calibrated to provide a desired level of muscle stimulation and patient discomfort. As described above, this delivery value is independent of variations in muscle response of individual patients.

Figure 2B:
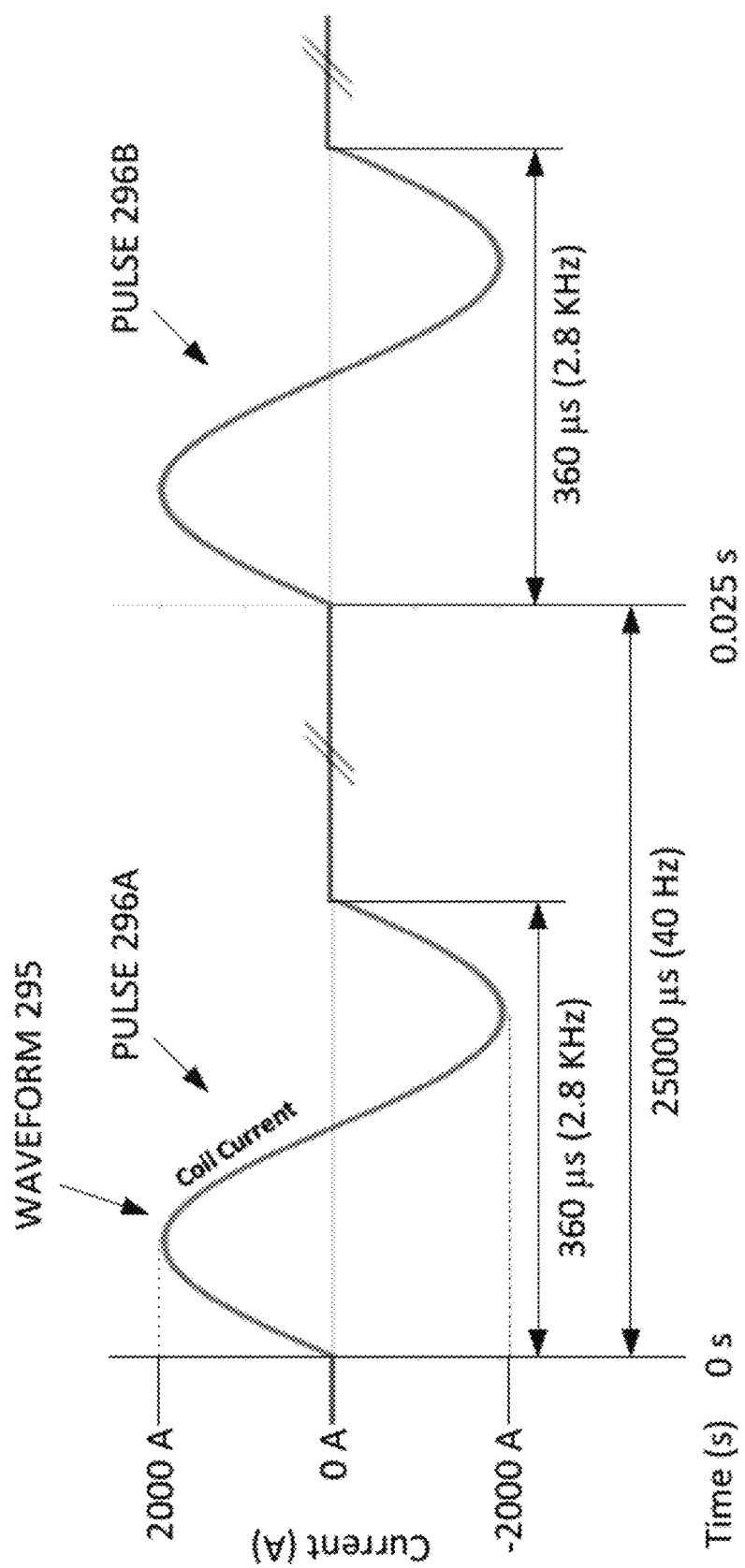
FIG. 2B depicts an example waveform to flow through coils of the electromagnetic applicator of FIG. 1C, according to various aspects of the subject technology.
Figure 2C:
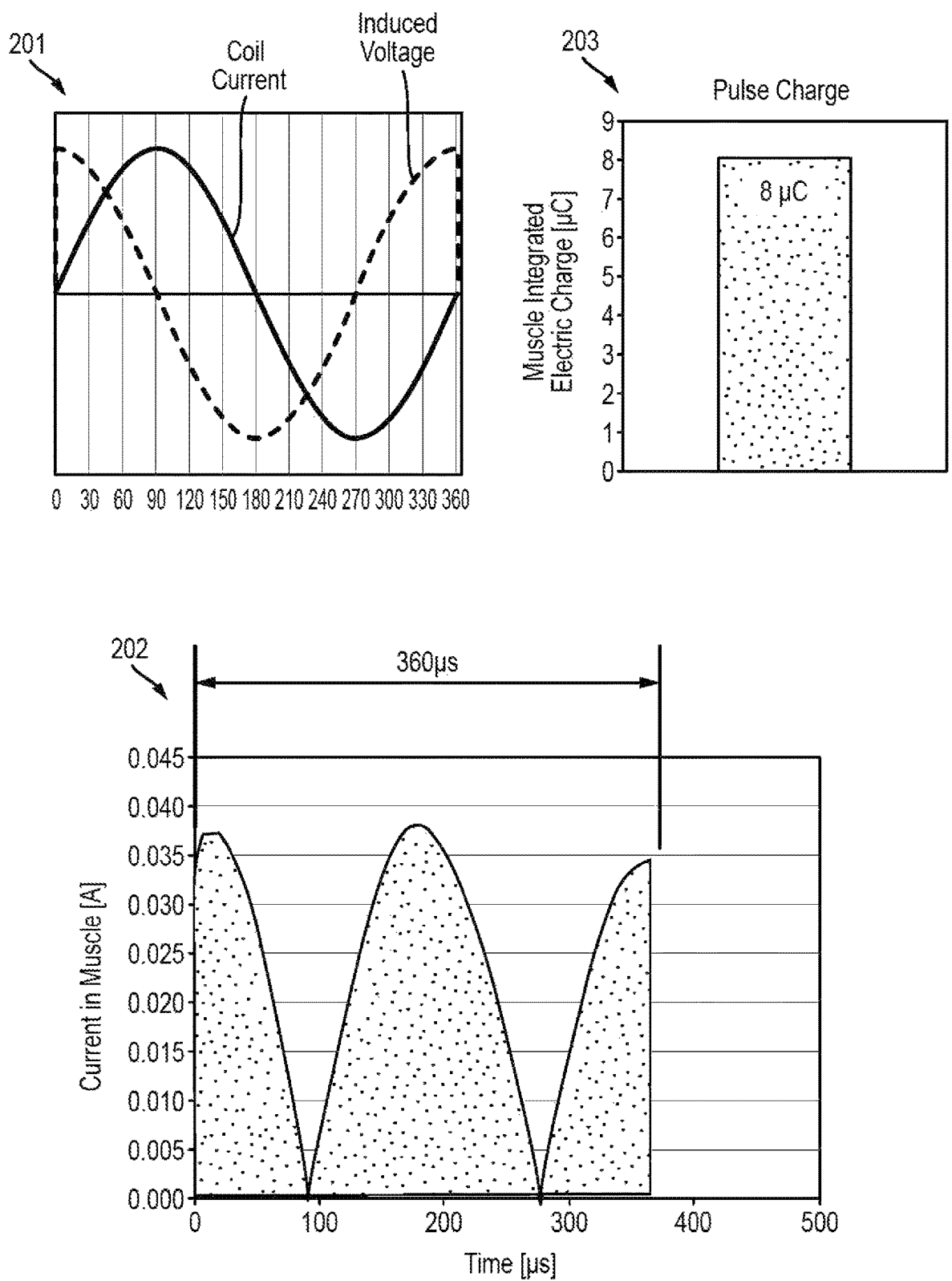
FIG. 2C depicts example measurements of current delivered to muscle tissues for a single pulse of the example waveform from FIG. 2B, according to various aspects of the subject technology.
Figure 2D:
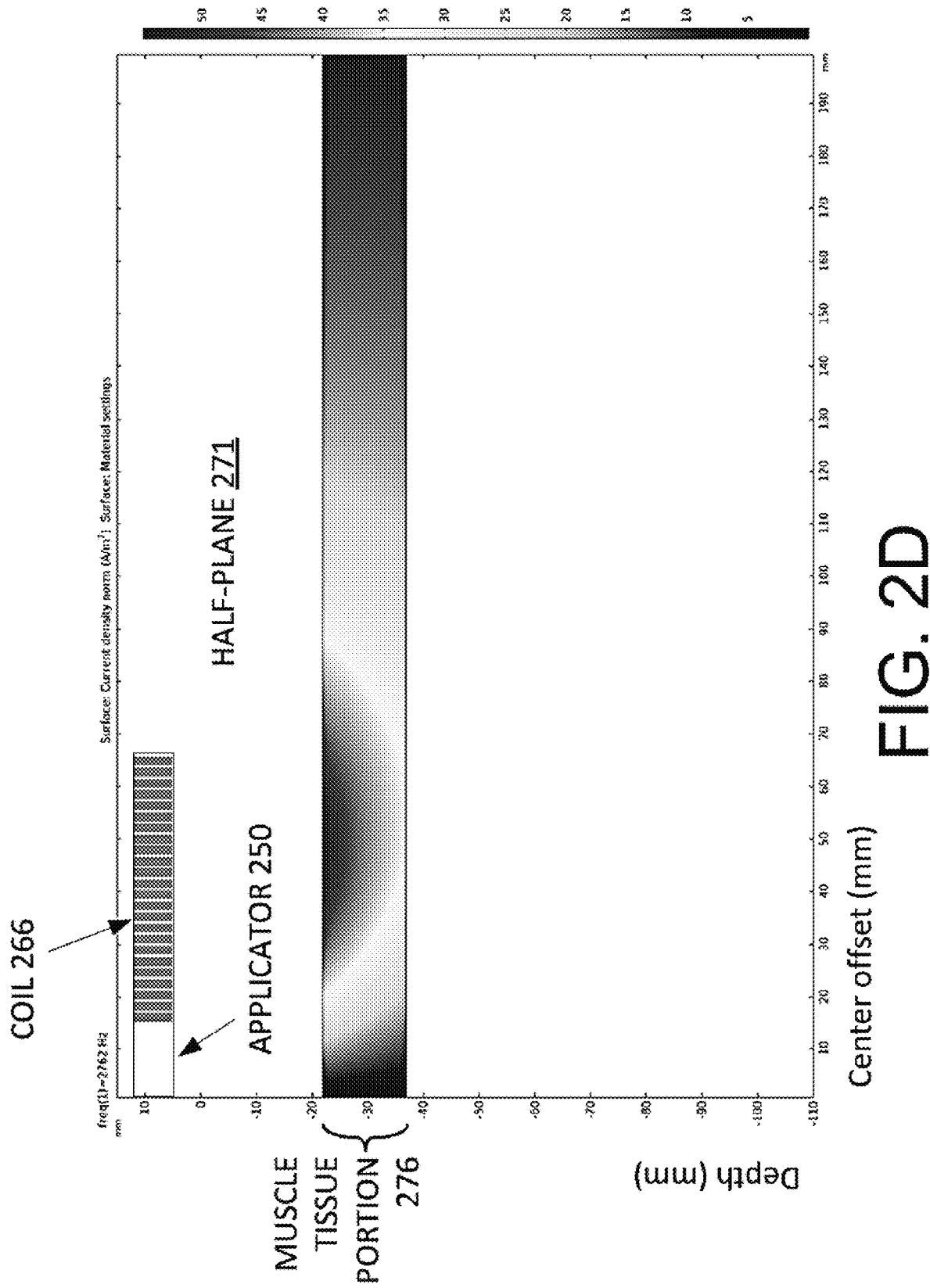
FIG. 2D depicts example measurements of current density norm in muscle tissues for a single pulse of the example waveform from FIG. 2B, according to various aspects of the subject technology.
Figure 2E:
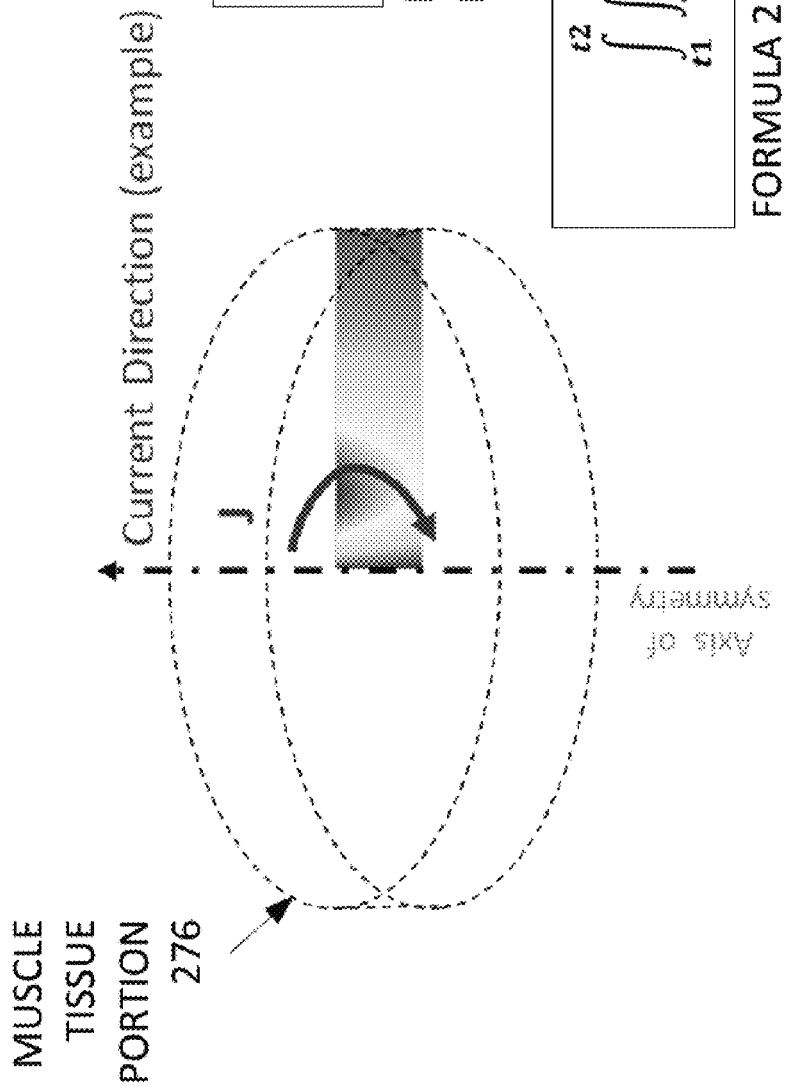
FIG. 2E depicts example calculations of induced current peak-to-peak and pulse charge for the example measurements of current density norm from FIG. 2D, according to various aspects of the subject technology.
Figure 2F:
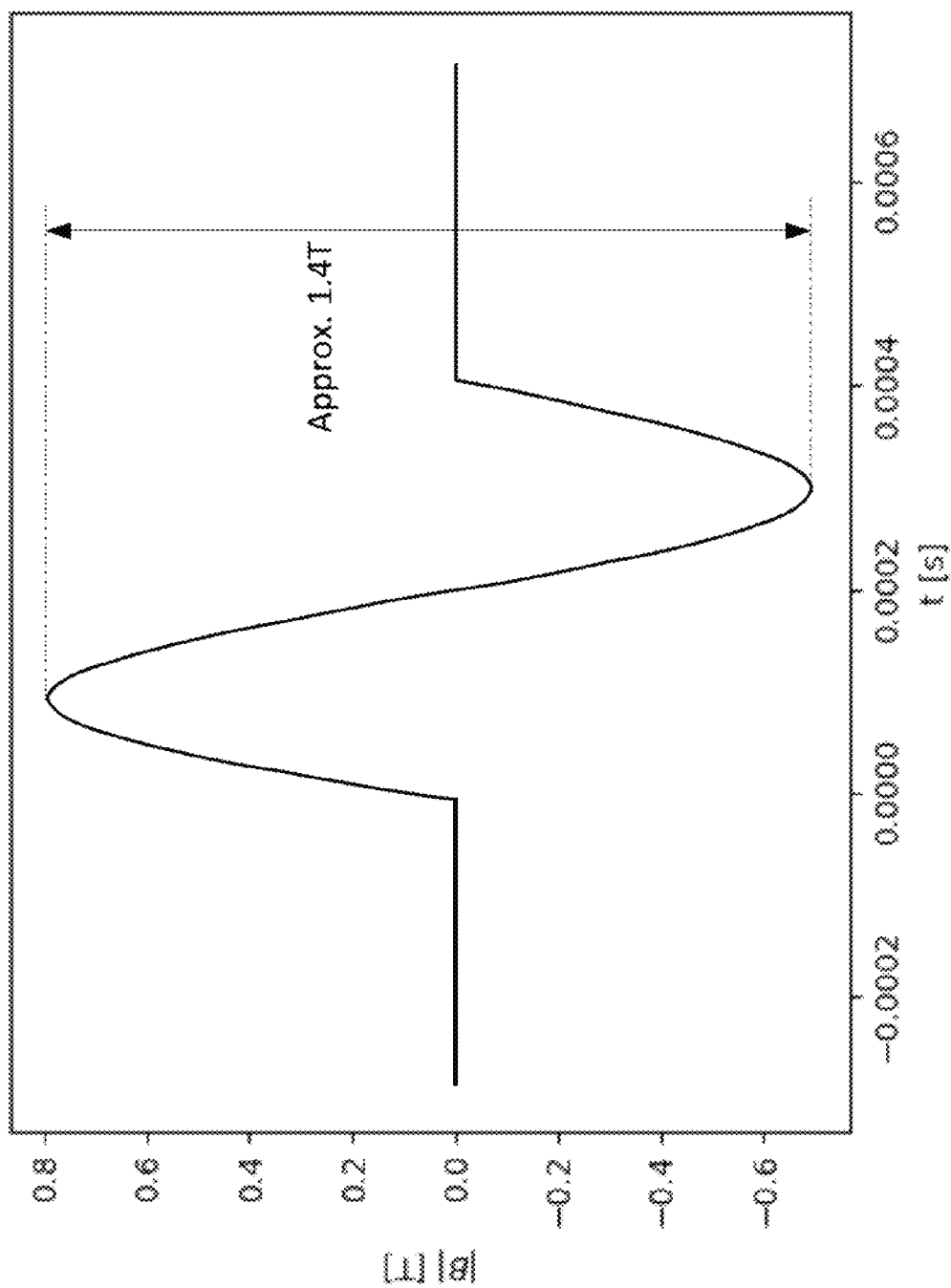
FIG. 2F depicts another example magnetic field waveform measurement resulting from a single pulse, according to various aspects of the subject technology, the waveform in FIG. 2F having a period of 400 microseconds, whereas the waveform in FIG. 2B has a period of 360 microseconds.
Figure 2G:
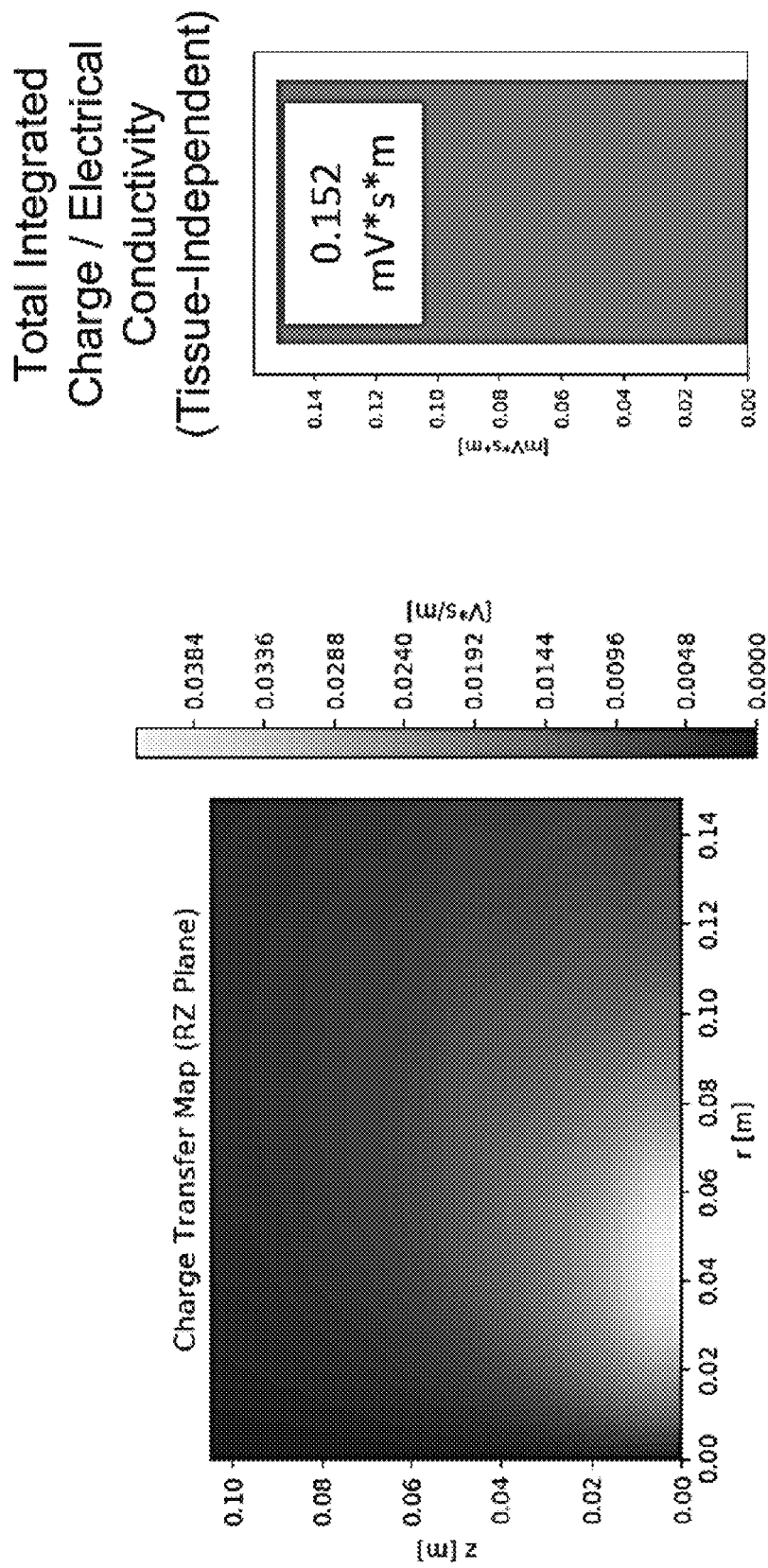
FIG. 2G depicts a charge transfer map resulting from a single pulse of the example waveform from FIG. 2F, according to various aspects of the subject technology.

The delivery value may be defined with respect to an arbitrary portion or volume limit, for example by limiting charge measurements to a cylinder extending 0.10 m deep from applicator surface 152 with an axis corresponding to the axis of coil 166 and a radius of 0.15 m, as shown in FIG. 2G. Of course, the specific volume limit used may vary. One method of calculating a delivery value with a volume limit is described below in conjunction with FIG. 2G. Since the induced charge may rapidly decline in proportion to distance, charge outside the volume limit may be assumed to be negligible or close to zero, and thus imposing a volume limit may facilitate calculation of the delivery value while still providing a reasonably accurate estimate.

A second value of delivery values 290, or maximum magnetic flux density, is defined to be 1.3 to 1.4 Tesla (T). In some implementations, the maximum magnetic flux density may be defined to be 1.2 to 1.5 T, 1.1 to 1.6 T, or 1.0 to 2.0 T. This value may be measured from a vertical plane, labelled the "XZ" plane, which may be defined to be perpendicular to both applicator surface 152 and handle 160. For example, the magnetic field at several points within the XZ plane may be measured as a pulse flows through coil 166. The point exhibiting the highest measurements can then be used to determine the maximum magnetic flux density, as shown in FIG. 2F.

A third delivery value, or maximum current density norm, is defined to be at least 40 amps per square meter (A/m2), and less than 100 A/m2. An example measurement is illustrated below in conjunction with FIG. 2D and FIG. 3A-3B.

A fourth delivery value, or induced current, peak-to-peak, is defined to be at least 70 milliamps (mA) and less than 200 mA. Example measurements are illustrated below in conjunction with FIG. 2E.

A parameter range 292 may be determined to generate delivery values 290, for example by experimental testing, model simulations, clinical testing, lookup tables, heuristics, or other methods. In some implementations, parameter range 292 may be a best effort range and not an exact match to satisfy delivery values 290. The parameter range 292 shown in FIG. 2A may satisfy the first parameter, or the delivery value being at least 0.115 mV*s*m. The ranges in parameter range 292 may be defined for each pulse of current flowing through coil 166. In the examples illustrated in the Figures, the current flowing through coil 166 is specifically defined to be an AC waveform that is sinusoidal and biphasic, as shown in FIG. 2B, and consists of a single 360 degree pulse for each muscle stimulation period (e.g., if the muscle stimulation frequency is 50 Hz, one 360 degree pulse is delivered 50 times a second). This treatment waveform includes a series of pulses, which cycle between high and low frequency portions, to cause polyphasic muscle stimulation in a patient, and more particularly triphasic stimulation. However, other waveforms may also be used. The pulses, as shown in FIG. 2B may be by their nature, discontinuous, but the induced magnetic field is continuously time-varying. At low stimulation frequency ranges of 0.5-10 Hz, for example, 2-10 Hz, preferably 3-10 Hz, used during the recovery session and the recovery portion of the treatment session, the pulses are sufficiently spaced to allow the muscle to recover but still high enough to provide a continuously pulsed time-varying magnetic field in the patient's tissue.

Referring to FIG. 2A, a first example parameter range 292 defines the pulse amplitude to be approximately 2000 amps (A). A second example parameter range 292 defines the pulse duration or width to be approximately 300-450 microseconds (μs), which corresponds to a frequency of approximately 2.2 to 3.3 kilohertz (KHz). A third example parameter range 292 defines a first waveform frequency (e.g., of the high frequency portion of the treatment waveform) to be approximately 10-50 pulses per second (pps). When the waveform is specifically an AC waveform, the pulse frequency can also be defined in hertz (Hz).

A combination of the first three parameter range 292, when combined with the electrical conductivity of the muscle being treated, defines a pulse charge per pulse, or integrated electric charge per pulse, of at least 6.4 microcoulombs (μC). This defines a total amount of electric charge or electrons that the muscle tissues receive for each pulse, as shown in conjunction with FIG. 2C below.

A fourth example parameter range 292 defines a second waveform frequency (e.g., of the low frequency portion of the treatment waveform) to be approximately 0.5-10 pps, for example, 1-10, 2-10, 3-10, 3-6, or 4-6 Hz. In some implementations, the second waveform frequency range may be set to 4, 5, or 6 Hz. In some implementations, the second waveform frequency may be set to a percentage or ratio of the first waveform frequency. For example, the second waveform frequency may be approximately 33% (⅓) or less, 25% (¼) of less, 20% (⅕) or less, 10% (1/10) or less, or 5% (1/20) or less of the first waveform frequency. However, it is preferable that the second waveform frequency is a non-zero number so that some stimulation is still provided. FIG. 2I, FIG. 2J, FIG. 2K contain tables showing three preferred treatment protocol examples which will now be explained.

Example 1: Abdomen

One treatment sequence includes a warm up session, one or more treatment sessions, one or more recovery sessions, and a cool down session. A 30-minute treatment of a patient's abdominal region, as shown in FIG. 2I, may begin with pulses having a low frequency of 5 Hz, lasting a duration of 10 seconds at 75% power, repeated twelve times (phase 1). Phase 1 corresponds to the warm up session of the treatment. After the warm up session, the first treatment session (Phase 2) includes pulses having a first high frequency portion of 25 Hz, for a duration of 5 seconds at 100% power, followed by a "recovery" portion having a frequency of 4 Hz for a duration of 6 seconds. The first high frequency portion of 25 Hz and the recovery portion of 4 Hz are repeated for 32 times in phase 2. Phase 3 corresponds to the recovery session, which is distinct from the recovery portion of Phase 2. Phase 3 includes pulses having a low frequency of 5 Hz, for a duration of 5 seconds at 75% power, repeated nine times. Phase 4 corresponds to the second treatment session, and repeats the parameters of Phase 2 for 31 times. Phase 5 corresponds to the second recovery session, and repeats the parameters of Phase 3 for ten times. Phase 6, which corresponds to the third treatment session, includes pulses having a second high frequency portion of 40 Hz, for a duration of 5 seconds at 80% power, followed by a "recovery" portion having a frequency of 4 Hz for a duration of 6 seconds. The second high frequency portion of 40 Hz and the recovery portion of 4 Hz are repeated for 31 times in Phase 6. Phase 7 corresponds to the third recovery session, and repeats the parameters of Phase 5 for 14 times. Phase 8 corresponds to the further treatment session, and repeats the parameters of Phase 6 for 28 times. Phase 9, Phase 10, and Phase 11 jointly form the cool down session. Phase 9 uses pulses having a low frequency of 5 Hz, for a duration of 10 seconds at 75% power, repeated eight times. Phase 10 uses pulses having a low frequency of 5 Hz, for a duration of 10 seconds at 60% power, repeated eight times. The treatment ends after phase 11, which involves pulses having a low frequency of 5 Hz for a duration of two seconds at 60% power. In Example 1, the treatment sequence includes four treatment sessions (Phases 2, 4, 6, and 8) three recovery sessions (Phases 3, 5, 7), one warm up session (Phase 1) and one cool down session (Phases 9-11). Pairs of treatment sessions are separated by a recovery session. The recovery sessions (Phases 3, 5, and 7) are different from the recovery portions of the treatment sessions. In this example, the number of iterations of recovery sessions (i.e., three) is fewer than the number of iterations of the recovery portions (i.e., 32 in the first treatment session, 31 in the second and third treatment sessions and 29 in the fourth treatment sessions). In other words, the low frequency pulses occur in two different low frequency waveforms within the treatment sequence—the recovery portion of the treatment session, and the recovery session.

Example 2: Buttocks

One treatment sequence includes a warm up session, one or more treatment sessions, one or more recovery sessions, and a cool down session. A 30-minute treatment of a patient's buttocks, as shown in FIG. 2J, may begin with pulses having a low frequency of 5 Hz, lasting a duration of 10 seconds at 75% power, repeated twelve times (phase 1). Phase 1 corresponds to the warm up session of the treatment. After the warm up session, the first treatment session (phase 2) includes uses pulses having a first high frequency portion of 18 Hz, for a duration of 5 seconds at 100% power, followed by a "recovery" portion having a frequency of 4 Hz for a duration of 6 seconds. The first high frequency portion of 18 Hz and the recovery portion of 4 Hz are repeated for 30 times in phase 2. Phase 3 corresponds to the recovery session, which is distinct from the recovery portion of Phase 2. Phase 3 includes pulses having a low frequency of 5 Hz, for a duration of 5 seconds at 75% power, repeated 13 times. Phase 4 corresponds to the second treatment session, and repeats the parameters of Phase 2 for 30 times. Phase 5 corresponds to the second recovery session, and repeats the parameters of Phase 3 for 13 times. Phase 6, which corresponds to the third treatment session, includes pulses having a second high frequency portion of 35 Hz, for a duration of 5 seconds at 80% power, followed by a "recovery" portion having a frequency of 4 Hz for a duration of 6 seconds. The second high frequency portion of 35 Hz and the recovery portion of 4 Hz are repeated for 30 times in Phase 6. Phase 7 corresponds to the third recovery session, and repeats the parameters of Phase 5 for 13 times. Phase 8 corresponds to the further treatment session, and repeats the parameters of Phase 6 for 30 times. Phase 9 and Phase 10 jointly form the cool down session. Phase 9 uses pulses having a low frequency of 5 Hz, for a duration of 10 seconds at 75% power, repeated twelve times. The treatment ends after phase 10, which involves pulses having a low frequency of 5 Hz lasting for a duration of 45 seconds at 60% power. In Example 2, the treatment sequence includes four treatment sessions (Phases 2, 4, 6, and 8) three recovery sessions (Phases 3, 5, 7), one warm up session (Phase 1) and one cool down session (Phases 9-10). Pairs of treatment sessions are separated by a recovery session. The recovery sessions (Phases 3, 5, and 7) are different from the recovery portions of the treatment sessions. In this example, the number of iterations of recovery sessions (i.e., three) is fewer than the number of iterations of the recovery portions (i.e., 30 in the first, second, third, and fourth treatment sessions). The low frequency pulses in Example 2 also occur in two different low frequency waveforms within the treatment sequence—the recovery portion of the treatment session, and the recovery session.

Example 3: Thighs

One treatment sequence includes a warm up session, one or more treatment sessions, one or more recovery sessions, and a cool down session. A 20-minute treatment of a patient's thighs, as shown in FIG. 2K, may begin with pulses having a low frequency of 5 Hz, lasting a duration of 10 seconds at 75% power, repeated nine times (Phase 1). Phase 1 corresponds to the warm up session of the treatment. After the warm up session, the first treatment session (Phase 2) includes pulses having a first high frequency portion of 20 Hz, for a duration of 5 seconds at 100% power, followed by a "recovery" portion having a frequency of 4 Hz for a duration of 6 seconds. The first high frequency portion of 18 Hz and the recovery portion of 4 Hz are repeated for 23 times in Phase 2. Phase 3 corresponds to the recovery session, which is distinct from the recovery portion of Phase 2. Phase 3 includes pulses having a low frequency of 5 Hz, for a duration of 5 seconds at 75% power, repeated 10 times. Phase 4 corresponds to the second treatment session, and repeats the parameters of Phase 2 for 23 times. Phase 5 corresponds to the second recovery session, and repeats the parameters of Phase 3 for 11 times. Phase 6, which corresponds to the third treatment session, includes pulses having a second high frequency portion of 30 Hz, for a duration of 6 seconds at 80% power, followed by a "recovery" portion having a frequency of 4 Hz for a duration of 6 seconds. The second high frequency portion of 30 Hz and the recovery portion of 4 Hz are repeated for 14 times in Phase 6. Phase 7 corresponds to the third recovery session, and repeats the parameters of Phase 5 for 12 times. Phase 8 corresponds to the further treatment session, and repeats the parameters of Phase 6 for 14 times. Phase 9 and Phase 10 jointly form the cool down session. Phase 9 uses pulses having a low frequency of 5 Hz, for a duration of 10 seconds at 75% power, repeated nine times. The treatment ends after phase 10, which involves pulses having a low frequency of 5 Hz lasting for a duration of 13 seconds at 60% power. In Example 3, the treatment sequence includes four treatment sessions (Phases 2, 4, 6, and 8) three recovery sessions (Phases 3, 5, 7), one warm up session (Phase 1) and one cool down session (Phases 9-10). Pairs of treatment sessions are separated by a recovery session. The recovery sessions (Phases 3, 5, and 7) are different from the recovery portions of the treatment sessions. In this example, the number of iterations of recovery sessions (i.e., three) is fewer than the number of iterations of the recovery portions (i.e., 23 in the first and second treatment sessions, 14 in the third and fourth treatment sessions). The low frequency pulses in Example 3 also occur in two different low frequency waveforms within the treatment sequence—the recovery portion of the treatment session, and the recovery session.

Figure 2H:
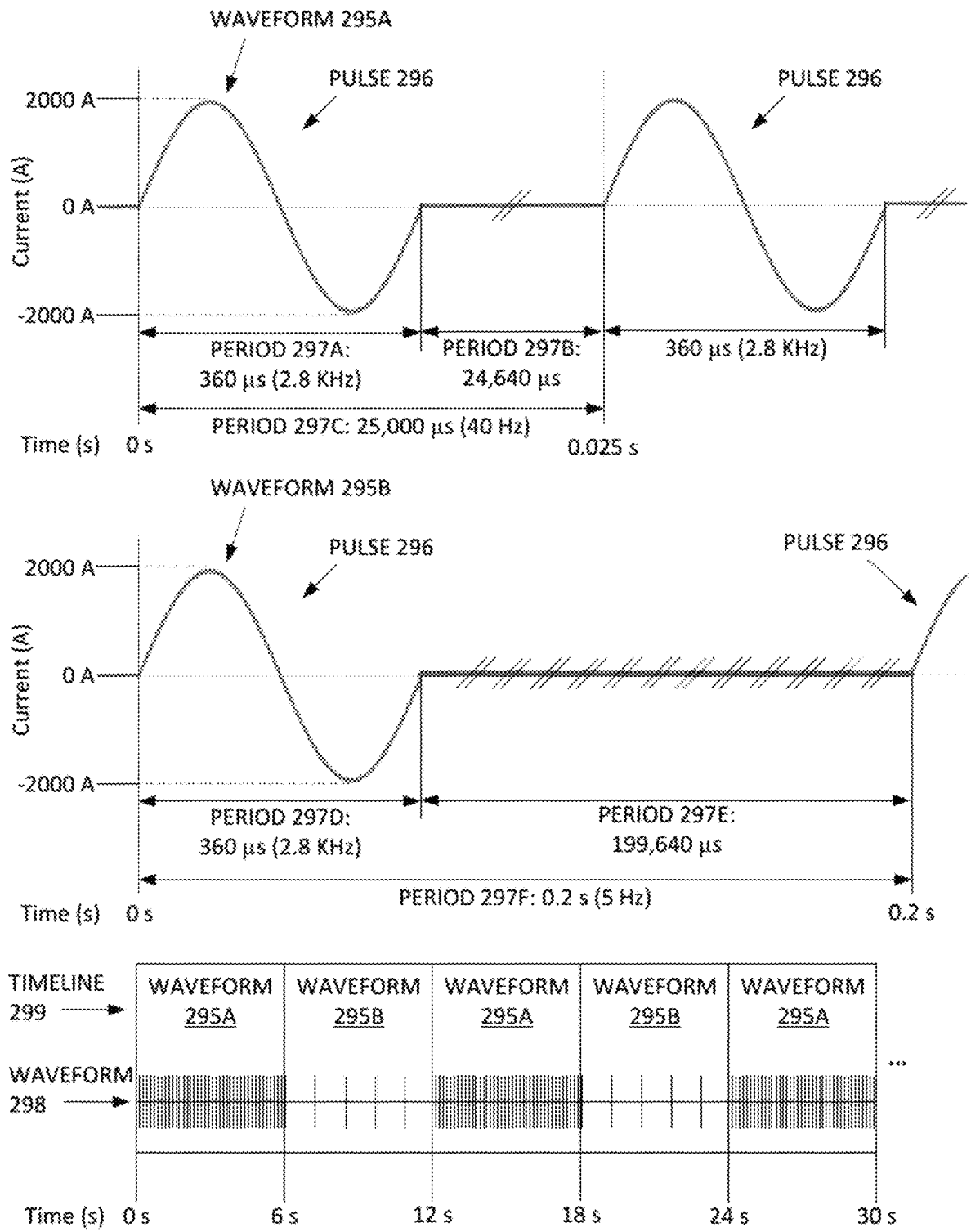
FIG. 2H depicts example alternating high frequency portions and low frequency portions of the treatment waveforms which flow through coils of the electromagnetic applicator of FIG. 1C, according to various aspects of the subject technology.
Figure 2L:
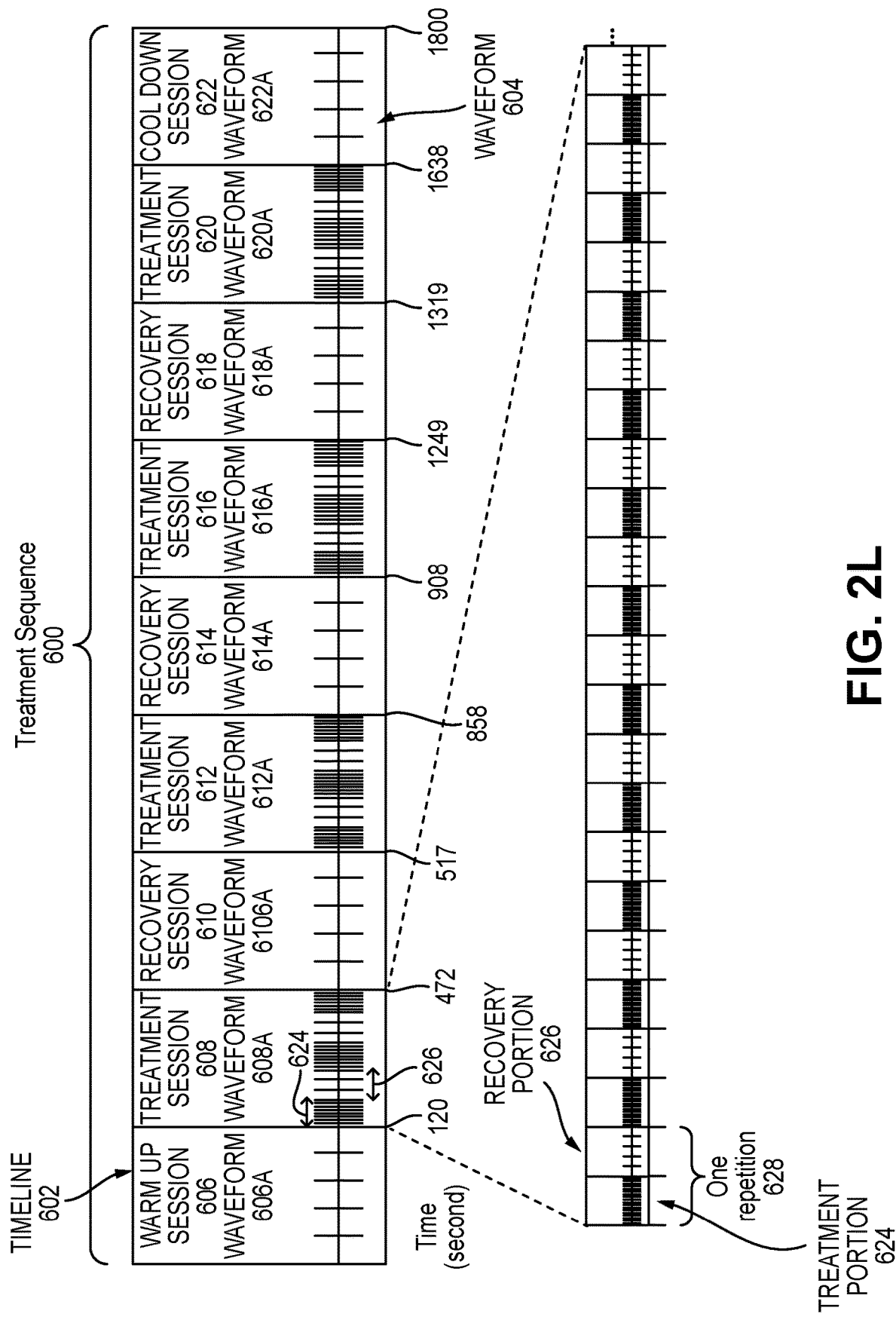
FIG. 2L depicts a schematic illustration of an example treatment sequence, according to various aspects of the subject technology.

FIG. 2L depicts a schematic illustration of an example treatment sequence, according to various aspects of the subject technology. A treatment sequence 600 has a timeline 602 that includes a warm up session 606, a first treatment session 608, a first recovery session 610, a second treatment session 612, a second recovery session 614, a third treatment session 616, a third recovery session 618, a fourth treatment session 620, and a cool down session 622.

As shown in timeline 602, waveforms 606A, 608A, 610A, 612A, 614A, 616A, 618A, 620A, and 622A may be output to generate waveform 604, which may be output into coil 166. The timeline 602 is not drawn to scale, and time values (in seconds) are the values used in Example 1 (FIG. 2I). The time values more clearly illustrate the typical ranges of duration of each session.

The treatment sessions 608, 612, 616, and 620 have treatment portions and recovery portions. For example, the waveform 608A in the first treatment session 608 has a treatment portion 624 and a recovery portion 626. Only a few iterations are schematically illustrated in the timeline 602 for each of the sessions. An expanded view of the waveform 608A is shown in the lower portion of FIG. 2L. Each treatment portion 624 is alternatingly followed by a recovery portion 626. One treatment portion 624 and one recovery portion 626 form one repetition 628. The expanded view shows only 12 iterations, whereas the first treatment session 608 in Example 1 (of FIG. 2I) has 32 iterations (or repetitions). The treatment sessions may have on the order of 30 iterations of a treatment portion and a recovery portion. The time duration of the treatment portion 624 and the time duration of the recovery portion 626 may be similar. In Example 1, the treatment portion 624 lasts for 5 seconds and the recovery portion 626 lasts for 6 seconds. The third treatment session 616 and the fourth treatment session 620 may have different waveform frequency in the treatment portion compared to the waveform frequency in the treatment portion of the first treatment session 608 and the second treatment session 612. In Example 1, the treatment portion in the third treatment session 616 is 40 Hz, while the treatment portion 624 in the first treatment session 608 is 25 Hz. Even though the waveform 610A in the first recovery session 610 appears to have more sparsely spaced pulses compared to the pulses in the recovery portion 626 of the treatment session, in Example 1, the waveform frequency of the first recovery session 610 is 5 Hz, and the waveform frequency of the pulses in the recovery portion 626 is 4 Hz.

Treatment sequence 600 shows that there is much more pulse activity in the treatment portion 626 of the treatment sessions compared to the recovery portion 626 and the waveforms 606A, 610A, 614A, 618A, and 622A. In this manner, continuous muscle stimulation can be provided with alternating periods of high intensity stimulation and low intensity stimulation.

The treatment portion 624 and the recovery 626 are each on the order of 5 or 6 seconds long, and are repeated on the order of 30 times to generate the treatment session 608. The treatment sessions 608, 612, 616, and 620 have no zero pulse segments. In other words, the waveform 608A, 612A, 616A and 620A do not include any 0 Hz rest periods. In addition, pulses are continuously delivered during the warm up session 606, all three recovery sessions 610, 614, and 618, and the cool down session 622. The treatment sessions 608, 612, 616, and 620 are separated by recovery sessions 610, 614, and 618, the recovery sessions lasting on the order of 60-100 seconds.

The low frequency waveforms 610A, 614A, and 618A, and the recovery portion 624 of the treatment sessions allow the patient's muscle and/or tissue to recover and/or relax. Such relaxation and recovery not only achieve the same goal as other systems and methods that utilize rest periods with 0 Hz frequency, but may also enhance the treatment process by delivering more pulses to the patient's muscle or tissues, during the recovery periods.

Using high and low frequencies rather than high and zero frequencies provides a continuously changing time-varying magnetic field in the muscle and elsewhere which provides continuous muscle stimulation. It has been found that continuous muscle stimulation provides better results than using rest periods with zero stimulation after delivering high frequency pulses. Further, some patients may better respond better to continuous stimulation, as rest periods with zero stimulation can be somewhat jarring and unexpected in comparison to continuous stimulation with different intensities. In this regard, the invention provides muscle stimulation with no "off" period or periods, thereby providing superior results compared to muscle stimulation that includes rest periods with zero stimulation. Substituting zero stimulation with low frequency stimulation also results in the muscle receiving more pulses (and hence induced electrical current and associated electrical charge) for a given total treatment time. In Example 1, as shown in FIG. 2I, 2952 pulses are provided during the recovery portions of the treatment sessions. In Example 2, as shown in FIG. 2J, 2880 pulses are provided during the recovery portions of the treatment sessions. In Example 3, as shown in FIG. 2K, 1776 pulses are provided during the recovery portions of the treatment sessions. In addition, it has been discovered that patients may respond better to treatment sequences with low frequency periods rather than zero frequency periods since they may "feel" that something is always happening in the muscle (and hence continuous improvement seems reasonable) as opposed to a treatment which is on/off where the off periods can seem like a bit of wasted time (especially if the off periods are relatively long).

Pulses having a frequency above 0.5 Hz generate a continuously time varying magnetic field regardless of how much the pulse frequency (corresponding to the inverse of the pulse duration, typically in the range of several kHz) exceeds the treatment (or waveform) frequency (e.g., 0.5-50 Hz). For treatment (or waveform) frequencies less than 15 Hz, the muscle has time to fully relax between each twitch caused by the pulses, which are less than 15 Hz. Because the muscle has time to fully relax between pulses having waveform frequencies that are less than 10 or 15 Hz, such periods can be used as a recovery period while still allowing additional pulses to be delivered to the patient's muscle and/or tissues. Hence, even though the recovery sessions (e.g., 610A, 614A, and 618A in FIG. 2L) and the recovery portion (e.g., 626 in FIG. 2L) are part of a recovery period, the methods and systems described herein allow more pulses/twitches to be delivered to the patient's muscle and tissues even during the recovery periods. Even though FIG. 2L shows multiple treatment sessions (e.g., each of Examples 1-3 uses four treatment sessions) separated by low frequency periods on the order of 60 seconds (e.g., the recovery sessions), in some implementations, a single relatively long treatment session may also be used. In such cases, the number of iterations in that single treatment session would increase by a factor of roughly 4. Thus, the number of iterations in a treatment session may be between 10-140.

The various treatment sessions in FIGS. 2I-2K have the durations of 352, 341, 319, 330, 253, 168 seconds. These examples include four treatment sessions. In some implementations, instead of four treatment sessions, a single treatment session may be approximately four times longer the ranges described in FIGS. 2I-2K. A preferred range for the upper limit of the length of the treatment session may be greater than any of 400, 500, 600, 700, 800, 1000, 1200, 1400, 1600, or 1800 seconds, and less than approximately 2000 seconds. A preferred range for the lower limit of the length of the treatment session greater than 50, 75, 100, 120, or 140 seconds and less than 160 seconds.

The waveform frequency of the treatment portion 624 of the treatment sessions may be between 10-50 Hz. In Examples 1-3, the waveform frequency of the treatment portion 624 are 18, 20, 25, 30, 35, 40 Hz. In some implementations, the waveform frequency of the treatment portion is between 15-50 Hz, for example 18-45 Hz, 20-40 Hz, or 25-40 Hz.

The waveform frequency of the recovery sessions and the recovery portion of the treatment session may be between 2-10 Hz. In Example 1-3, the waveform frequency of the recovery sessions and the recovery portion of the treatment session are 5 Hz and 4 Hz, respectively. In some implementations, the waveform frequency of the recovery sessions and the recovery portion of the treatment session are 3-10 Hz, for example 3-8 Hz, 3-6 Hz, 4-8 Hz, 4-6 Hz, 5-7 Hz, or 4-5 Hz.

A method for strengthening, toning, and firming muscle tissues includes receiving parameters for operation of a magnetic muscle stimulation device (100), the magnetic muscle stimulation device (100) includes a device applicator (150) having a coil (166) positioned in a housing (164) of the device applicator (150), an axis of the coil substantially perpendicular to an applicator surface of the housing. The parameters include a first waveform frequency (624) of 10-50 Hz; a second waveform frequency (626) of 2-10 Hz; a third waveform frequency of between 2-10 Hz (610A, 614A, 618A); a pulse duration of 300-450 microseconds; and an individual pulse frequency of 2.2-3.3 kHz, the individual pulse frequency being substantially higher than the first waveform frequency. The method includes causing, based on receiving the parameters, a first alternating current having one or more first pulses to flow for a first length of time through the coil according to the first waveform frequency, wherein each of the one or more pulses has the pulse duration of 300-450 microseconds and the individual pulse frequency of 2.2-3.3 kHz. The method also includes causing, following the first length of time, a second alternating current having one or more second pulses to flow through the coil for a second length of time according to the second waveform frequency that is lower than the first waveform frequency, wherein each of the one or more second pulses has the pulse duration of 300-450 microseconds and the individual pulse frequency of 2.2-3.3 kHz. The method includes repeating the causing of the first and second alternating currents for a plurality of iterations to provide a continuously pulsed time-varying magnetic field that alternates between the first and the second waveform frequencies, wherein the first length of time is 2-12 seconds, and the second length of time is 2-12 seconds, and the plurality of iterations is 10-140 iterations, thereby generating a treatment session (608, 612, 616, 620). The method includes causing, based on receiving the parameters, a third alternating current having one or more third pulses to flow through the coil for a third length of time according to the third waveform frequency, thereby generating a recovery session (610, 614, 618). Each of the one or more third pulses has the pulse duration of 300-450 microseconds and the individual pulse frequency of 2.2-3.3 kHz, the third length of time is 30-80 seconds. The method includes generating a plurality of the treatment sessions (608, 612, 616, 620), a pair of adjacent treatment sessions (608, 612) being separated by the recovery session (610). The first, second, and third waveform frequencies (624, 626, and 610A) provide a continuously pulsed time-varying magnetic field that alternates between the first, second and third waveform frequencies.

A fifth example parameter range 292 defines a duration of each high frequency portion of the duty cycle and low frequency portion of the duty period to fall within 2-12 seconds. For example, the high frequency portion of the duty cycle and the low frequency portion of the duty cycle may be repeated in an alternating, round-robin fashion for a number of iterations, with the sum of the iterations creating a treatment session. It has been found that 4-10 seconds for each high frequency portion and low frequency portion provides an optimal time for sufficient continuous stimulation and recovery or relaxation (during which additional stimulation is provided) of muscles to provide more efficient muscle stimulation overall. Further, the iterations may be set to a specific total number of iterations, such as 8-200 iterations, such as 10-140, or 8-40 iterations, which may result in a therapy session that lasts for approximately 15 to 30 minutes. The number of iterations may be set depending on muscle strengthening and toning goals. As explained above in reference to FIGS. 2I-2K, each of Examples 1-3 include roughly 4 treatment sessions. Each treatment session includes a treatment portion having a high frequency component and a recovery portion having a low frequency component. Pairs of treatment sessions are separated by a recovery session. The number of iterations of the recovery sessions (three recovery sessions in each of Examples 1-3) is fewer than the number of iterations of the recovery portions in each treatment session (which is on the order of 30). The low frequency pulses in Examples 1-3 occur in two different low frequency waveforms within the treatment sequence—the recovery portion of the treatment session, and the recovery session.

A sixth example parameter range 292 defines a ratio between the high frequency portion of the duty cycle and the low frequency portion of the duty cycle. In the example shown in FIG. 2A, the ratio is defined not to exceed 6:4 and not to fall below 4:6. In other words, the time periods are calibrated to be close to each other, as it has been found that significantly different time periods for the high frequency portion and low frequency portion of the duty cycle are less effective.

As shown in parameter set 294A and parameter set 294B, specific parameter values may be set within the ranges defined by parameter range 292. For example, referring to parameter set 294A for the high frequency portion of the duty cycle, pulse amplitude may be set to 2000 A, pulse duration or width may be set to 360 µs (for a pulse frequency of approx. 2.8 KHz), and waveform frequency may be set to 40 Hz. The resulting pulse charge may be measured to be 8 µC. In some implementations where waveforms other than sinusoidal biphasic AC are used, alternate waveform shapes and parameters may also be defined. The values in parameter set 294A may be predetermined and retrieved from non-volatile storage or may be calculated on the fly based on predetermined or adjustable delivery values 290. Optionally, parameter set 294A may be selected and/or adjusted based on input received from human interface device 126.

Parameter set 294B for low frequency portion of the duty cycle may be set or programmed in a similar fashion as parameter set 294A. As shown in FIG. 2A, pulse amplitude may be set to 2000 A, pulse duration or width may be set to 360 µs (for a pulse frequency of approx. 2.8 KHz), and waveform frequency may be set to 5 Hz. As discussed above, the second (low frequency portion of the duty cycle) waveform frequency may be a percentage or ratio of the first (high frequency portion of the duty cycle) waveform frequency. In this case, the second waveform frequency (5 Hz) is 12.5% of the first waveform frequency (40 Hz). As seen in parameter sets 294A-249B, lengths of the low frequency portion and the high frequency portion of the duty cycle are both set to 6 seconds, for a 1:1 (or 5:5) ratio.

FIG. 2B depicts an example waveform 295 using parameter set 294A to flow through coil 166, according to various aspects of the subject technology. As shown in FIG. 2B, pulse 296A and pulse 296B both satisfy parameter set 294A, which defines a pulse amplitude of 2000 A, a pulse width of 360 µs (2.8 KHz), and a first waveform frequency of 40 Hz. Waveform 295 may continue repeating such that 40 pulses satisfying parameter set 294A are generated in one second, thereby satisfying the defined first waveform frequency of 40 Hz. It should be noted that FIG. 2B may not be drawn to scale to more clearly illustrate the waveform shapes of each pulse.

FIG. 2C depicts example measurements of current in muscle tissues for pulse 296A from FIG. 2B, according to various aspects of the subject technology. As shown in chart 201 of FIG. 2C, the coil current of pulse 296A generates an induced voltage (dotted line) into muscle tissue. The total current delivered to muscle tissues as a result of the induced voltage from pulse 296A is measured against time in chart 202. By calculating the area under the curve in chart 202, or the muscle integrated electric charge, a pulse charge of approximately 8 µC may be determined as shown in chart 203, which readily exceeds the minimum 6.4 µC pulse charge of parameter range 292 set forth in FIG. 2A. However, since the pulse charge may vary depending on individual muscle responses of different patients, it would be preferable to use a tissue-independent value to measure the efficacy of applicator 150 when using pulses defined by parameter set 294A. A process for determining such a tissue-independent value is illustrated in conjunction with FIG. 2G below.

FIG. 2D depicts example measurements of current density norm in muscle tissue portion 276 within half plane 271 for pulse 296A from FIG. 2B, according to various aspects of the subject technology. As shown in FIG. 2D and FIG. 2E, muscle tissue portion 276 is defined by a cylindrical cross section with a radius of approximately 200 mm at a depth of approximately 22 mm to 37 mm below a skin layer of a patient. Applicator 250 is placed such that the bottom surface of coil 266 is approximately 5 mm above and parallel to a skin surface layer of a patient, which may be assumed to be at depth 0 mm. Of course, the specific cross sectional portion used for muscle tissue portion 276 may be arbitrarily defined to include the majority of electrical activity occurring in muscle tissue. Further, it should be understood that the depicted diagrams are idealized approximations, as the skin surface will not be perfectly flat in a real world measurement.

When the windings 168 of coil 166 are precision constructed and tightly wound, the resulting magnetic field may be highly axisymmetric when coil 166 is energized. Thus, the magnetic field may be treated as axisymmetric to simplify calculations. The center offset may be defined relative to the axis of symmetry perpendicular to applicator surface 152, as shown in FIG. 2E. Thus, the left side edge of half-plane 271 is aligned with the center of coil 266. Due to the symmetry, only the positive plane, or half-plane 271, may be considered for integral calculations of muscle tissue portion 276.

Due to the inherent electrical properties of muscle tissue, muscle tissue more readily conducts induced electrical current from electromagnetic sources, such as coil 166 of applicator 150. Conversely, fat and nerve cells do not as readily conduct electrical current from electromagnetic sources (fat and nerve cells have higher electrical resistance), allowing applicator 150 to selectively target muscle tissue portion 276 with induced electrical currents and charge created by the changing magnetic and electrical fields. FIG. 2D shows the current density norm for muscle tissue portion 276 in an example patient according to induced current caused by pulse 296A flowing through coil 166. As shown in FIG. 2D, the portions closest to windings 168, or the portions near center offsets 20 mm to 80 mm, receive the highest current density norm, which may exceed 40 A/m2 to satisfy the third value of delivery values 290. The highest current density norm may be less than 100 A/m2.

FIG. 2E depicts example calculations of induced current peak-to-peak and pulse charge for the example measurements of current density norm from FIG. 2D, according to various aspects of the subject technology. As discussed above, since the magnetic field may be assumed to be axisymmetric, the formulas for determining the induced current peak-to-peak (Formula 1) and the pulse charge (Formula 2) can be simplified, as shown in FIG. 2E. By using Formula 1, the induced current peak-to-peak may be determined to be 70 milliamps (mA), satisfying the fourth value of delivery values 290. By using Formula 2, the pulse charge may be determined to be 8 μC, satisfying the range of at least 6.4 μC defined in parameter range 292 and consistent with the measurements shown in FIG. 2C.

FIG. 2F depicts an example magnetic field waveform measurement resulting from a pulse 296A having a period of 400 microseconds, according to various aspects of the subject technology. The magnetic field B may be measured against time at the XZ plane perpendicular to applicator surface 152 and handle 160. As shown in FIG. 2F, the maximum magnetic flux density is measured peak-to-peak to be approximately 1.4 T, satisfying the second value of delivery values 290.

FIG. 2G depicts a charge transfer map resulting from pulse 296A from FIG. 2F, according to various aspects of the subject technology. As discussed above, the magnetic field B can be assumed to be axisymmetric, in which case the XZ plane can also be interpreted to be the RZ plane, as the radius can be made equivalent to the X coordinate. To obtain the data points shown in FIG. 2G, several readings (e.g. 300 or more readings) may be taken across the RZ plane at depths 0 m to 0.10 m from applicator surface 152, as shown. Since the magnetic field B is assumed to be axisymmetric, only the positive half-plane may be considered in the charge transfer map, since the positive half-plane may be simply doubled to include the contribution of the negative half-plane. To calculate the total integrated charge/electrical conductivity from the charge transfer map, Faraday's law may be utilized, which may be expressed in integral form for axisymmetric systems:

$$E_\theta(r) = \frac{-1}{2\pi r} \int_0^r \frac{\partial B_z}{\partial t} 2\pi r \, dr$$

Formula 3: Faraday's law in integral form for axisymmetric systems.

For a device using a 400 microsecond pulse (FIG. 2F), |Eθ(r)| may be integrated with respect to time to generate the charge transfer map shown in FIG. 2G, which measures the charge, or volt seconds per meter (V*s/m) along the RZ plane. To calculate the tissue-independent total integrated charge/electrical conductivity or the delivery value, the charge transfer map may be integrated with respect to the RZ half-plane, resulting in 0.152 mV*S*m for z depth 0 m to 0.10 m, radius r=0.15 m, as shown. This is consistent with the first value of delivery values 290, or a tissue-independent total integrated charge/electrical conductivity of at least 0.115 mV*s*m.

FIG. 2H depicts example alternating high frequency portions and low frequency portions of the treatment waveforms 295A, 295B which flow through the coil(s) 166 of applicator 150, according to various aspects of the subject technology. As shown in FIG. 2H, waveform 295A for the high frequency portion of the duty cycle is the same as waveform 295 from FIG. 2B. It is understood, however, that a different waveform may be generated. As shown in the example of FIG. 2H, period 297A is 360 μs long and corresponds to the pulse width of pulse 296. Each period 297A is followed by period 297B (24,640 μs) within each waveform period. The period 297B contains no waveform. The sum of the period 297A and the period of 297B equal period 297C (25,000 μs), which corresponds to a high frequency value of 40 Hz. While only a single pulse is shown in period 297A, some implementations may use multiple pulses during the period 297C. Even though the period 297B contains no waveform, a time varying magnetic field is generated during the entire period 297C due to the pulse 296 generated in the period 297A. In fact, the pulse 296 in the period 297A generates a time-varying field in the tissue over the entire period 297C, no matter how short in pulse duration or how high in frequency (e.g., many kHz) the pulse 296 is. This applies to both the high frequency portion (10-50 Hz) of the treatment session as well as the low frequency portion (0.5-10 Hz) of the recovery portion in the treatment session and the recovery session.

Pulses having a frequency above 0.5 Hz generate a continuously time varying magnetic field regardless of how much the pulse frequency (corresponding to the inverse of the pulse duration, typically in the range of several kHz) exceeds the treatment (or waveform) frequency (e.g., 0.5-50 Hz). For treatment (or waveform) frequencies less than 15 Hz, the muscle has time to fully relax between each twitch caused by the pulses, which are less than 15 Hz. Because the muscle has time to fully relax between pulses having waveform frequencies that is less than 10 or 15 Hz, such periods can be used as a recovery period while still allowing additional pulses to be delivered to the patient's muscle and/or tissues. Hence, even though the recovery sessions (e.g., 610A, 614A, and 618A in FIG. 2L) and the recovery portion (e.g., 626 in FIG. 2L) are part of a recovery period, the methods and systems described herein allow more pulses/twitches to be delivered to the patient's muscle and tissues even during the recovery period.

When the treatment frequency is between 15-25 Hz, or 15-40 Hz, the tension in the muscle builds up with each twitch and the muscle may not relax between twitches. At frequencies above 40 Hz, the build-up of tension may be very rapid.

On the other hand, according to various implementations, waveform 295B for the low frequency portion of the duty cycle has a much slower waveform frequency of 5 pulses per second (5 Hz). Thus, each pulse 296 having period 297D is separated by period 297F, or 0.2 seconds of time, and period 297E (199,640 μs) during which there are no pulses is much longer compared to period 297B (24,640 μs). Note that the same pulse 296 may be used in both waveforms 295A and 295B. Thus, period 297A is the same as period 297D. However, some implementations may use different pulses for each waveform.

As shown in timeline 299, waveforms 295A and 295B may be output in an alternating, round-robin fashion to generate waveform 298, which may be output into coil 166. Waveform 298 helps to illustrate a difference in intensity between waveform 295A and 295B, wherein waveform 295A has much more pulse activity compared to waveform 295B. In this manner, continuous muscle stimulation can be provided with alternating periods of high intensity stimulation and low intensity stimulation, rather than using a recovery period with no stimulation after high intensity treatment. Having recovery periods with zero pulses provides the tissue with fewer pulses than having instead low frequency waveforms 295B.

Figure 3A:
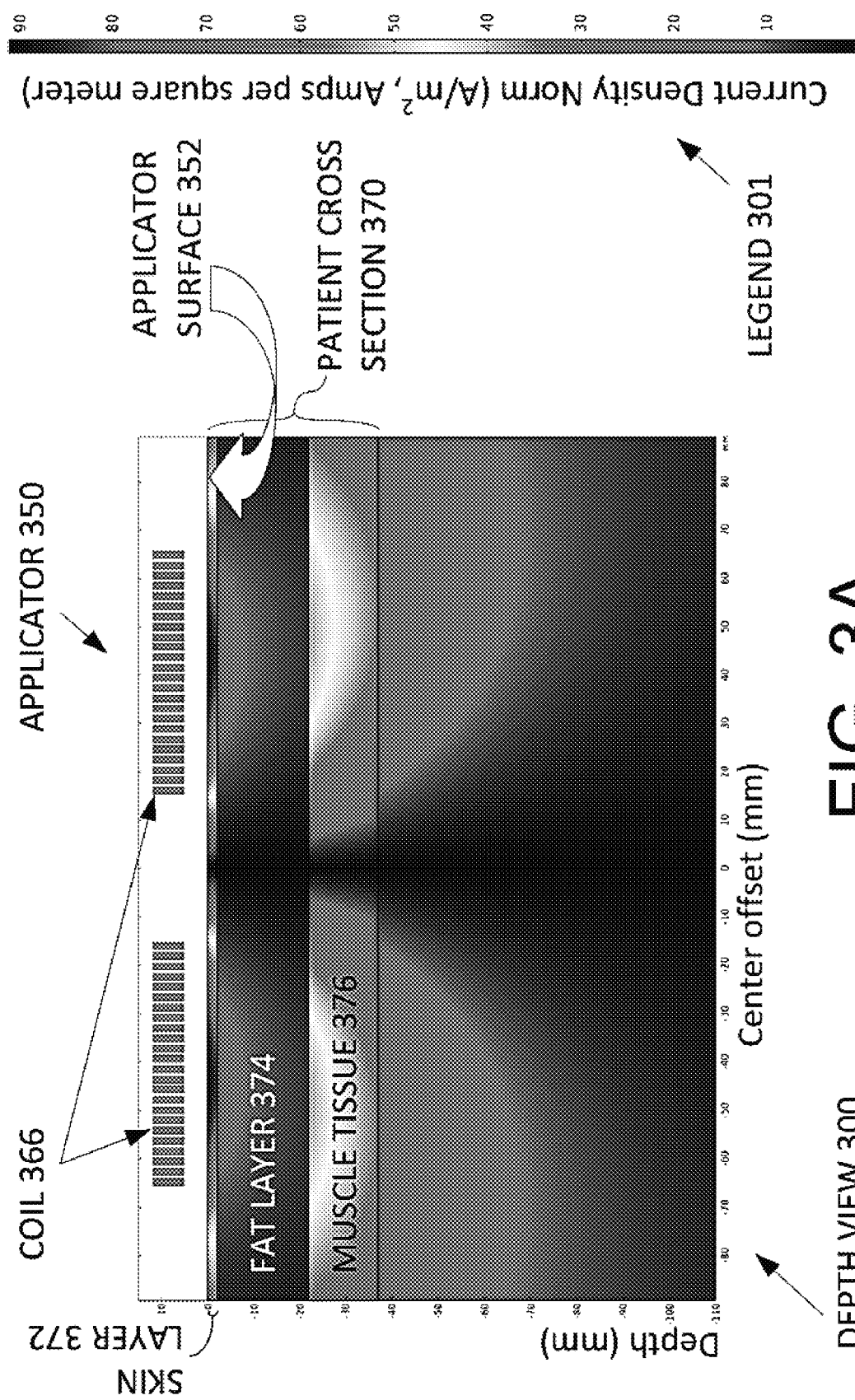
FIG. 3A and FIG. 3B respectively depict depth view and plane views of current density in a patient while using the electromagnetic applicator of FIG. 1C, according to various aspects of the subject technology.
Figure 3B:
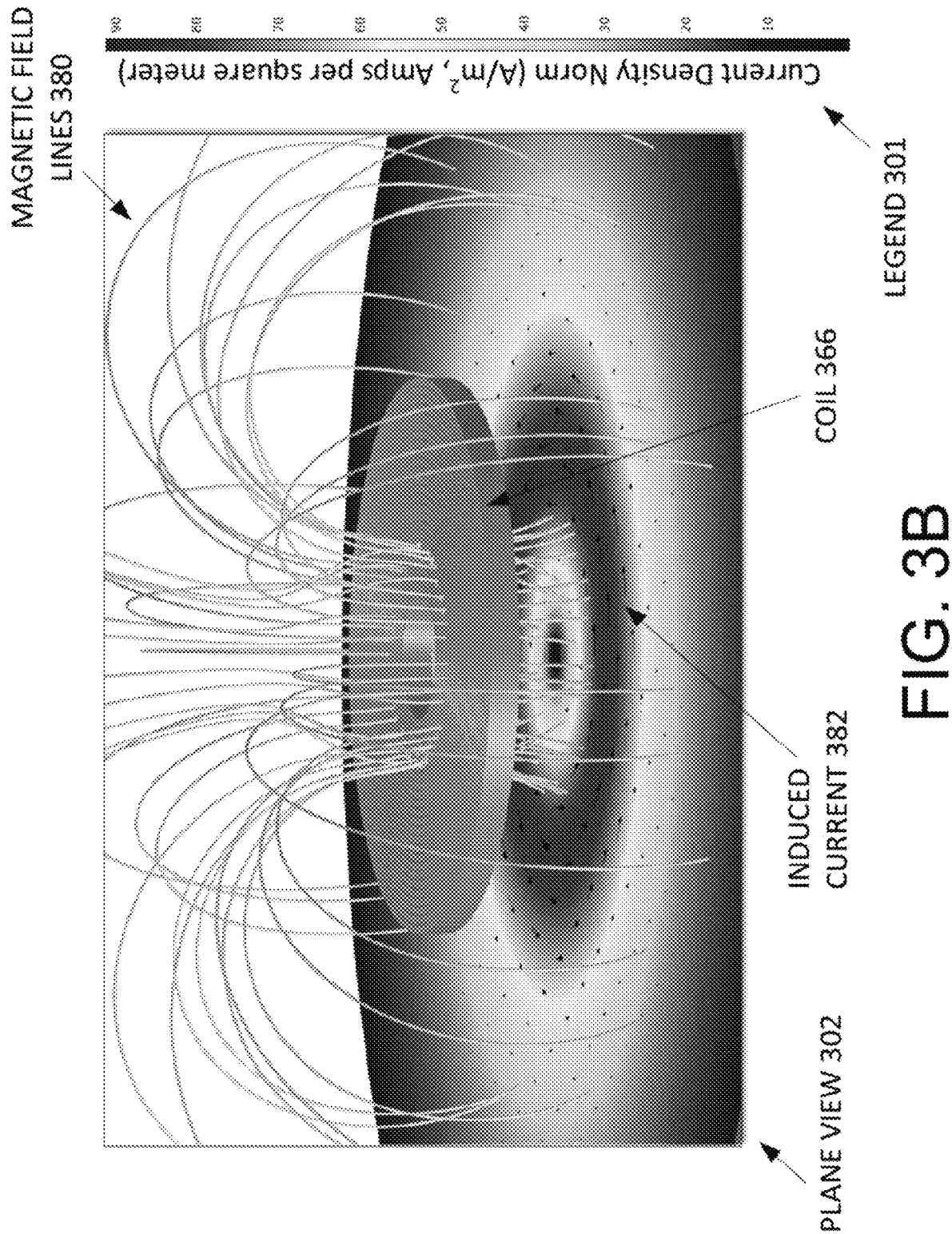

FIG. 3A and FIG. 3B respectively depict depth view 300 and plane view 302 of current density in an example patient while using applicator 350, according to various aspects of the subject technology. Applicator 350 includes coil 366 and applicator surface 352. FIG. 3A also includes legend 301 and patient cross section 370. Patient cross section 370 includes skin layer 372, fat layer 374, and muscle tissue 376. With respect to FIG. 3A and FIG. 3B, elements may correspond to like numbered elements from previous figures. For example, applicator 350 may correspond to applicator 150 from FIG. 1A-1D.

FIG. 3A may more clearly illustrate the selective application of current to muscle tissue 376. As shown in FIG. 3A, applicator 350 may be positioned such that applicator surface 352 is above and substantially parallel with skin layer 372. Coil 366 may be energized using parameter set 294A from FIG. 2A. As shown in depth view 300 and legend 301, due to the physical properties of fat layer 374 and muscle tissue 376, muscle tissue 376 may conduct current much more easily compared to fat layer 374, as indicated by the difference in current density.

Plane view 302 of FIG. 3B may correspond to a surface layer of skin layer 372. As shown in plane view 302, an axis of coil 366 may be substantially perpendicular to applicator surface 352. Magnetic field lines 380 are illustrated as being generated from coil 366. Of course, the individual field lines are only shown for exemplary purposes to illustrate the magnetic field. The magnetic field lines 380 cause a current to be induced in skin layer 372, as illustrated by induced current 382. A similar induced current is also generated in muscle tissue 376, but with reduced current density due to further distance from coil 366. As shown in FIG. 3B, the arrows indicate that induced current 382 is travelling counter-clockwise in the instant captured by the figure. It will be appreciated that the induced current 382 oscillates between counter-clockwise and clockwise as the coil is energized in an AC manner.

Figure 3C:
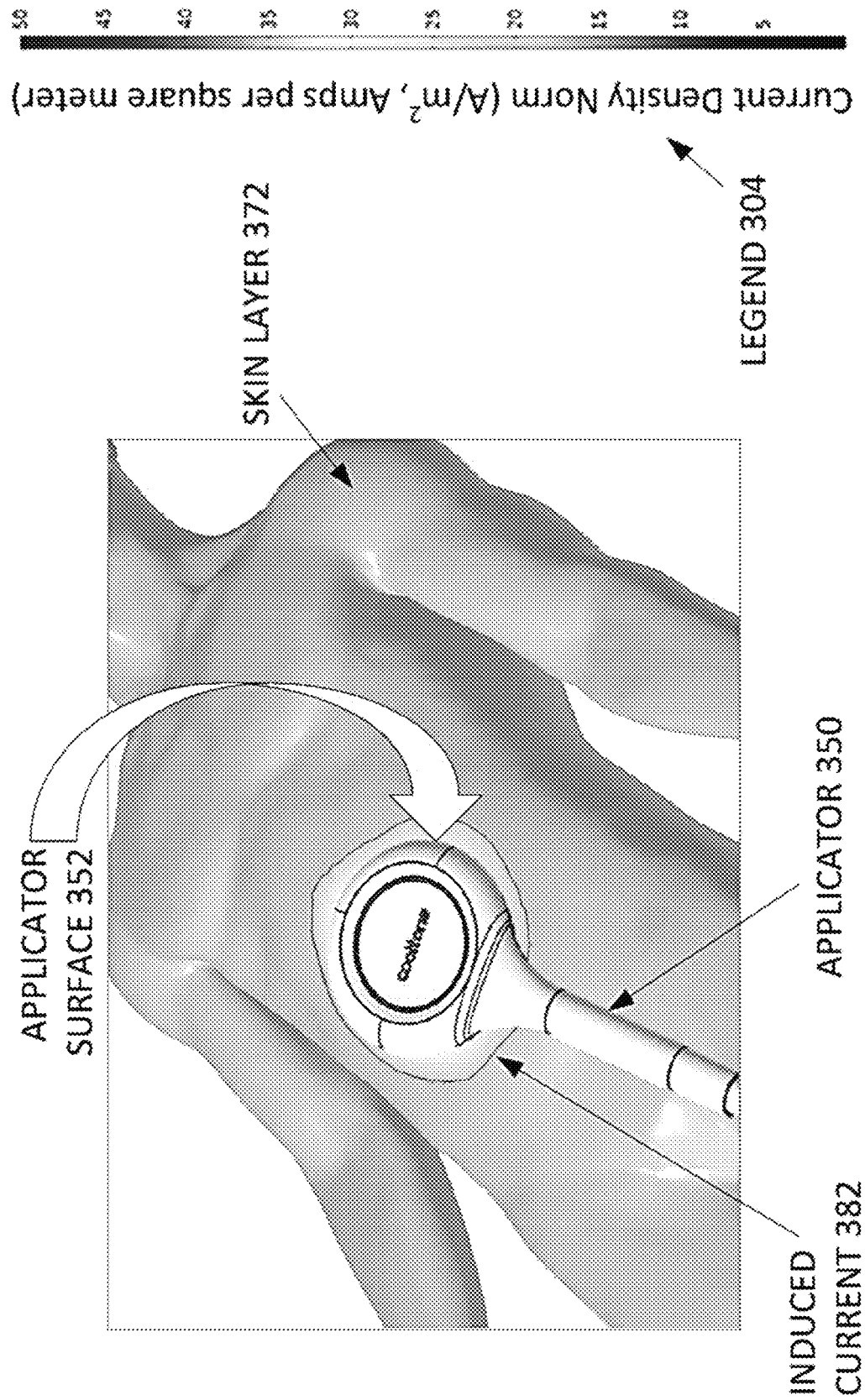
FIG. 3C and FIG. 3D depict overhead views of current density in a patient while using the electromagnetic applicator of FIG. 1C, according to various aspects of the subject technology.
Figure 3D:
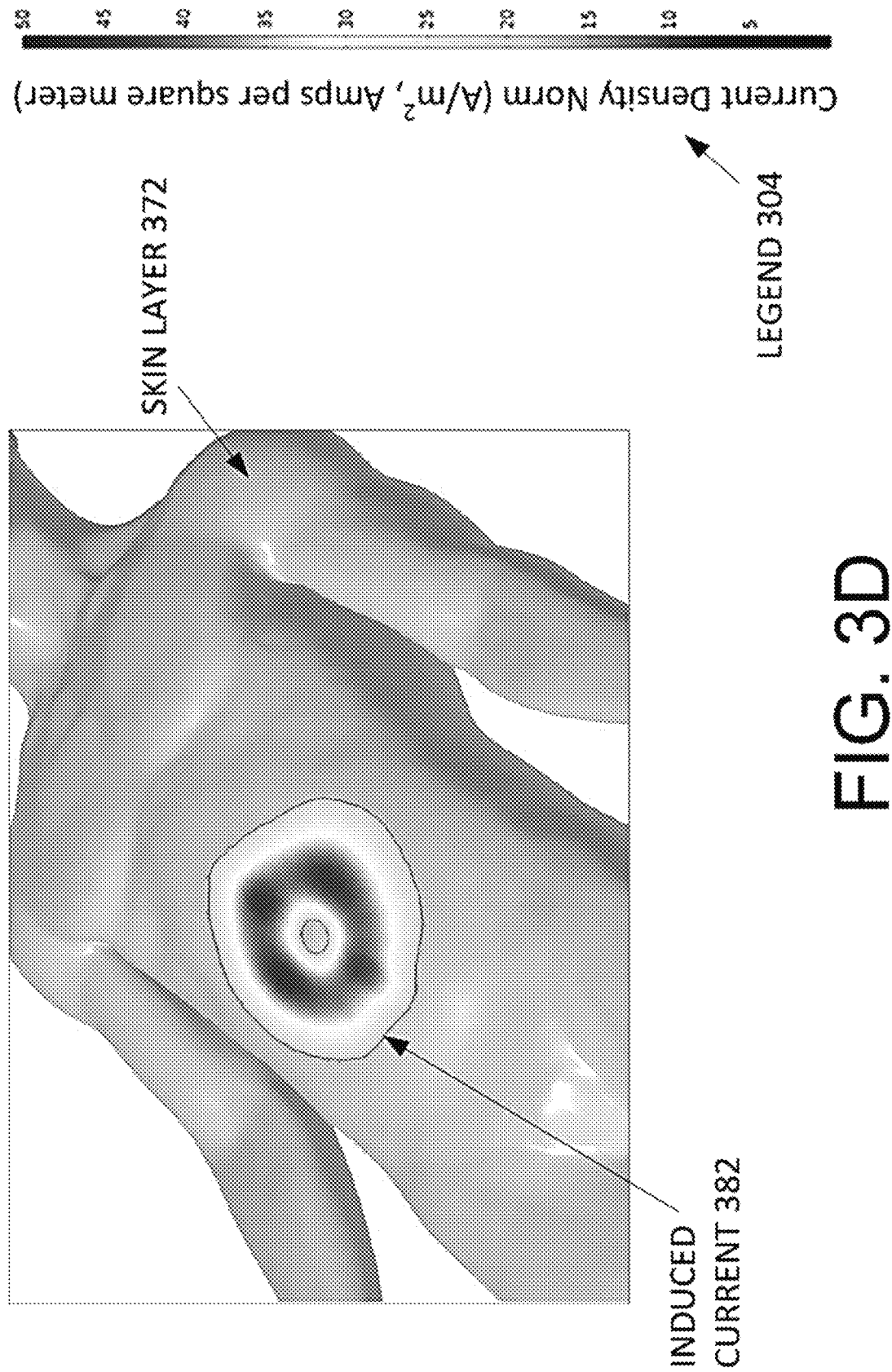

FIG. 3C and FIG. 3D depict overhead views of current density in a patient while using applicator 350 from FIG. 3A and FIG. 3B, according to various aspects of the subject technology. As shown in FIG. 3C, applicator surface 352 may be placed approximately parallel to the surface of skin layer 372, since skin layer 372 may not be uniformly flat due to individual body anatomy. To more clearly illustrate induced current 382, FIG. 3D omits applicator 350. As shown in FIG. 3D, induced current 382 may have a maximum current density of approximately 45 A/m2, satisfying the third value of delivery values 290.

FIG. 4 depicts an example process 400 for using alternating high frequency portions and low frequency portions of the treatment waveforms to deliver effective amounts of electromagnetic charge to muscle tissues, according to various aspects of the subject technology. For explanatory purposes, the various blocks of example process 400 are described herein with reference to FIGS. 1A-3D, and the components and/or processes described herein. The one or more of the blocks of process 400 may be implemented, for example, by a computing device, including a processor and other components utilized by the device. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, parameters are received for operation of a magnetic muscle stimulation device comprising a device applicator having a coil positioned in a housing of the device applicator, an axis of the coil substantially perpendicular to an applicator surface of the housing (411). Referring to FIG. 1A, this may correspond to processor 122 receiving parameters 190 for operation of applicator 150. Referring to FIG. 1C and FIG. 1D, applicator 150 has a coil 166 in housing 164. Referring to FIG. 3A and FIG. 3B, the applicator 350 corresponding to applicator 150 has a coil 366 wherein an axis of coil 366 is substantially perpendicular to applicator surface 352.

As previously described, parameters 190 (FIG. 1A) may be predetermined, or may be set according to user input received from human interface device 126. Using the example shown in FIG. 2A, parameters 190 in process 400 (FIG. 4) may correspond to satisfying the first value of delivery value 290, or providing a tissue-independent integrated electric charge/electrical conductivity of at least 0.115 mV*s*m. In turn, a parameter range 292 may be determined to satisfy delivery values 290, and a specific parameter set 294A and 294B of parameter values may be determined to satisfy parameter range 292. As shown in FIG. 2A, parameter set 294A and 294B may include a first waveform frequency (40 Hz), a pulse frequency (2.8 KHz) that is substantially higher than the first waveform frequency (2.8 KHz>40 Hz), and a second waveform frequency (5 Hz) that is non-zero and substantially lower than the first waveform frequency (5 Hz<40 Hz).

Processor 122 may continue to cause, based on the received parameters, a first alternating current to flow for a first length of time through a coil of the applicator according to the first waveform frequency, where one or more current pulses are generated at the pulse frequency (412) For example, referring to FIG. 1A, FIG. 2A and FIG. 2H, this may correspond to processor 122 causing, based on parameter set 294A and 294B, an alternating current to flow for 6 seconds through coil 166 of applicator 150 according to waveform 295A having a first waveform frequency of 40

Hz, wherein each period 297C of waveform 295A comprises period 297A in which pulse 296 is generated at 2.8 KHz followed by period 297B. In this manner, a continuously pulsed time-varying magnetic field that alternates between the first and the second waveform frequencies is generated. As explained above, pulses having a frequency above 0.5 Hz generate a continuously time varying magnetic field regardless of how much the pulse frequency (corresponding to the inverse of the pulse duration, typically in the range of several kHz) exceeds the treatment (or waveform) frequency (e.g., 0.5-50 Hz). For treatment (or waveform) frequencies less than 15 Hz, the muscle has time to fully relax between each twitch caused by the pulses, which are less than 15 Hz. Because the muscle has time to fully relax between pulses having waveform frequencies that is less than 10 or 15 Hz, such periods can be used as a recovery period while still allowing additional pulses to be delivered to the patient's muscle and/or tissues. Hence, even though the recovery sessions (e.g., 610A, 614A, and 618A in FIG. 2L) and the recovery portion (e.g., 626 in FIG. 2L) are part of a recovery period, the methods and systems described herein allow more pulses/twitches to be delivered to the patient's muscle and tissues even during the recovery period.

Processor 122 may continue to cause, following the first length of 6 seconds, a second alternating current to flow through the coil of the applicator for a second length of time according to the second waveform frequency (413). For example, referring to FIG. 1A, FIG. 2A and FIG. 2H, this may correspond to processor 122 causing, following the first output of waveform 295A on timeline 299, a second alternating current to flow through for 6 seconds according to waveform 295B having a second waveform frequency of 5 Hz, wherein waveform 295B comprises a plurality of pulses 296 generated at 5 Hz.

Processor 122 may determine whether further iterations are remaining (414). If yes, then process 400 returns to block 412 after block 413. If no, then process 400 ends.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
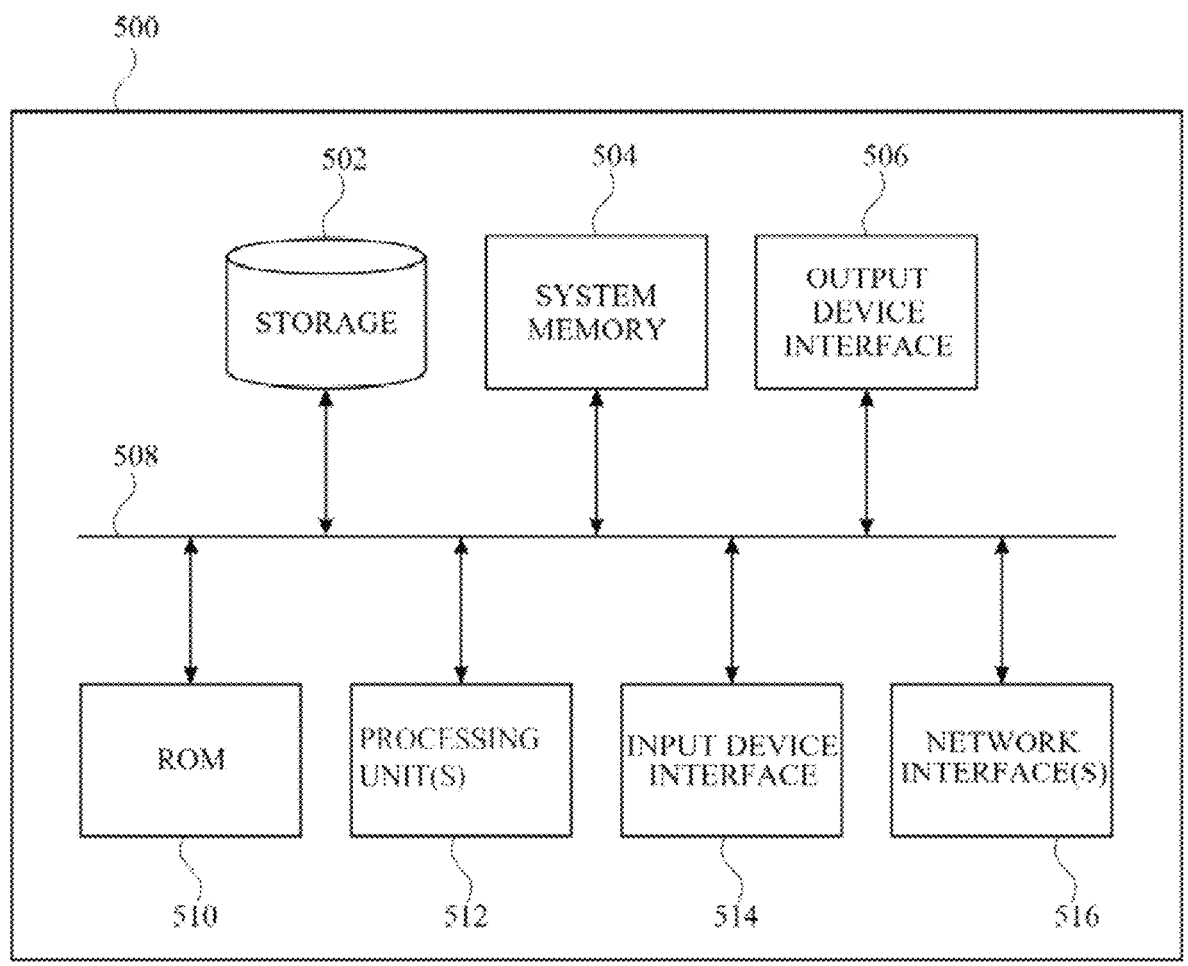
FIG. 5 is a conceptual diagram illustrating an example electronic system for using alternating high frequency portions and low frequency portions of the treatment waveforms to deliver effective amounts of electromagnetic charge to muscle tissues, according to various aspects of the subject technology.

FIG. 5 is a conceptual diagram illustrating an example electronic system 500 for using alternating high frequency portions and low frequency portions of the treatment waveforms to deliver effective amounts of electromagnetic charge to muscle tissues, according to various aspects of the subject technology. Electronic system 500 may be a computing device for execution of software associated with one or more portions or steps of process 400, or components and processes provided by FIGS. 1A-4. Electronic system 500 may be representative, in combination with the disclosure regarding FIGS. 1A-4, of the base unit 120 and/or the applicator 150 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Some implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism.

The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method for strengthening, toning, and firming muscle tissues, the method comprising:
  receiving parameters for operation of a magnetic muscle stimulation device, the magnetic muscle stimulation device comprising a device applicator having a coil positioned in a housing of the device applicator, an axis of the coil substantially perpendicular to an applicator surface of the housing, wherein the parameters include:
    a first waveform frequency in the range of 10-50 Hz;
    a second waveform frequency in the range of 2-10 Hz, wherein the second waveform frequency is lower than the first waveform frequency;
    a third waveform frequency in the range of 2-10 Hz;
    a pulse duration in the range of 300-450 microseconds; and
    an individual pulse frequency in the range of 2.2-3.3 kHz;
  causing, based on receiving the parameters, a first alternating current having one or more first pulses to flow for a first length of time through the coil according to the first waveform frequency, wherein each of the one or more first pulses has the pulse duration in the range of 300-450 microseconds and the individual pulse frequency in the range of 2.2-3.3 kHz;

causing, following the first length of time, a second alternating current having one or more second pulses to flow through the coil for a second length of time according to the second waveform frequency that is lower than the first waveform frequency, wherein each of the one or more second pulses has the pulse duration in the range of 300-450 microseconds and the individual pulse frequency in the range of 2.2-3.3 kHz;

repeating the causing of the first and second alternating currents for a plurality of iterations to provide a continuously pulsed time-varying magnetic field that alternates between the first and the second waveform frequencies, wherein the first length of time is between 2-12 seconds, and the second length of time is between 2-12 seconds, and the plurality of iterations is between 10-140 iterations, thereby generating a treatment session having a length of between 100-1000 seconds;

causing, based on receiving the parameters, a third alternating current having one or more third pulses to flow through the coil for a third length of time according to the third waveform frequency, thereby generating a recovery session, wherein each of the one or more third pulses has the pulse duration in the range of 300-450 microseconds and the individual pulse frequency in the range of 2.2-3.3 kHz, and the third length of time is between 30-80 seconds, and generating a plurality of the treatment sessions, a pair of adjacent treatment sessions being separated by the recovery session;

wherein the first, second, and third waveform frequencies provide a continuously pulsed time-varying magnetic field that alternates between the first, second and third waveform frequencies, and wherein a magnetic flux density generated by the magnetic muscle stimulation device is between 1.2-2.0 tesla (T), an inductance of the coil is between 30-50 micro Henry (mH), and the coil has an inner diameter between 0-50 mm and an outer diameter of between 50-150 mm.

2. The method of claim 1, further comprising:

causing, based on receiving the parameters, a fourth alternating current having one or more fourth pulses to flow through the coil for a fourth length of time according to a fourth waveform frequency in the range of 2-10 Hz, thereby generating a warm up session;

causing, based on receiving the parameters, a fifth alternating current having one or more fifth pulses to flow through the coil for a fifth length of time according to a fifth waveform frequency in the range of 2-10 Hz, and generating the warm up session prior to the treatment and recovery sessions, and a cool down session following the treatment and recovery sessions, wherein the first, second, third, fourth, and fifth waveform frequencies provide a continuously pulsed time-varying magnetic field that alternates between the first, second, third, fourth, and fifth waveform frequencies.

3. The method of claim 1, wherein the second waveform frequency is either 10% (1/10), 25% (1/4), or 33% (1/3) or less than the first waveform frequency.

4. The method of claim 1, wherein the second waveform frequency is approximately 5 Hz or less.

5. The method of claim 1, wherein a ratio of the first length of time to the second length of time does not exceed 6:4 or fall below 4:6.

6. The method of claim 1, wherein the second length of time is longer than the first length of time, and the first waveform frequency is approximately in the range of 18 to 40 hertz (Hz).

7. The method of claim 1, wherein at least one of the first or second waveforms has a sinusoidal or biphasic waveform.

8. A magnetic muscle stimulation device for strengthening, toning, and firming muscle tissues, the magnetic muscle stimulation device comprising:

a device applicator comprising a housing having a substantially flat applicator surface, and a coil positioned in the housing with an axis of the coil substantially perpendicular to the applicator surface; and a processor configured to:
receive parameters including:
a first waveform frequency in the range of 10-50 Hz;
a second waveform frequency in the range of 2-10 Hz, wherein the second waveform frequency is lower than the first waveform frequency;
a third waveform frequency in the range of 2-10 Hz;
a pulse duration in the range of 300-450 microseconds; and
an individual pulse frequency in the range of 2.2-3.3 kHz;

cause, based on receiving the parameters, a first alternating current having one or more first pulses to flow for a first length of time through the coil according to the first waveform frequency, wherein each of the one or more first pulses has the pulse duration in the range of 300-450 microseconds and the individual pulse frequency in the range of 2.2-3.3 kHz;

cause, following the first length of time, a second alternating current having one or more second pulses to flow through the coil for a second length of time according to the second waveform frequency that is lower than the first waveform frequency, wherein each of the one or more second pulses has the pulse duration in the range of 300-450 microseconds and the individual pulse frequency in the range of 2.2-3.3 kHz; and repeat the causing of the first and second alternating currents for a plurality of iterations to provide a continuously pulsed time-varying magnetic field that alternates between the first and the second waveform frequencies, wherein the first length of time is between 2-12 seconds, and the second length of time is between 2-12 seconds, and the plurality of iterations is between 10-140 iterations, thereby generating a treatment session having a length of between 100-1000 seconds;

cause, based on receiving the parameters, a third alternating current having one or more third pulses to flow through the coil for a third length of time according to the third waveform frequency, thereby generating a recovery session, wherein each of the one or more third pulses has the pulse duration in the range of 300-450 microseconds and the individual pulse frequency in the range of 2.2-3.3 kHz, and the third length of time is between 30-80 seconds; and generate a plurality of the treatment sessions, a pair of adjacent treatment sessions being separated by the recovery session;

wherein the first, second, and third waveform frequencies provide a continuously pulsed time-varying magnetic field that alternates between the first, second and third waveform frequencies, and wherein a magnetic flux density generated by the magnetic muscle stimulation device is between 1.2-2.0 tesla (T), an inductance of the coil is between 30-50 micro Henry (mH), and the coil has an inner diameter between 0-50 mm and an outer diameter of between 50-150 mm.

9. The magnetic muscle stimulation device of claim 8, wherein the processor is configured to further:
cause, based on receiving the parameters, a fourth alternating current having one or more fourth pulses to flow through the coil for a fourth length of time according to a fourth waveform frequency in the range of 2-10 Hz, thereby generating a warm up session;
cause, based on receiving the parameters, a fifth alternating current having one or more fifth pulses to flow through the coil for a fifth length of time according to a fifth waveform frequency in the range of 2-10 Hz, and
generate the warm up session prior to the treatment and recovery sessions, and a cool down session following the treatment and recovery sessions, wherein
the first, second, third, fourth, and fifth waveform frequencies provide a continuously pulsed time-varying magnetic field that alternates between the first, second, third, fourth, and fifth waveform frequencies.

10. The magnetic muscle stimulation device of claim 8, wherein the processor is configured to receive parameters including the second waveform frequency as either being 10% ($\frac{1}{10}$), 25% ($\frac{1}{4}$), or 33% ($\frac{1}{3}$) or less than the first waveform frequency.

11. The magnetic muscle stimulation device of claim 8, wherein the processor is configured to receive parameters including the second waveform frequency as being approximately 5 Hz or less.

12. The magnetic muscle stimulation device of claim 8, further comprising a cover that is removably attachable to the device applicator, wherein the cover prevents contact of the device applicator with a patient's skin or clothing, while the magnetic muscle stimulation device is strengthening, toning, and firming the muscle tissues of the patient.

13. A non-transitory computer-readable medium comprising a plurality of instructions that, when read by a computing system, causes the computing system to perform a method of strengthening, toning, and firming muscle tissues, the method comprising:
receiving parameters for operation of a magnetic muscle stimulation device, the magnetic muscle stimulation device comprising a device applicator having a coil positioned in a housing of the device applicator, an axis of the coil substantially perpendicular to an applicator surface of the housing, wherein the parameters include:
a first waveform frequency in the range of 10-50 Hz;
a second waveform frequency in the range of 2-10 Hz, wherein the second waveform frequency is lower than the first waveform frequency;
a third waveform frequency in the range of 2-10 Hz;
a pulse duration in the range of 300-450 microseconds; and
an individual pulse frequency in the range of 2.2-3.3 kHz;
causing, based on receiving the parameters, a first alternating current having one or more first pulses to flow for a first length of time through the coil according to the first waveform frequency, wherein each of the one or more first pulses has the pulse duration in the range of 300-450 microseconds and the individual pulse frequency in the range of 2.2-3.3 kHz;
causing, following the first length of time, a second alternating current having one or more second pulses to flow through the coil for a second length of time according to the second waveform frequency that is lower than the first waveform frequency, wherein each of the one or more second pulses has the pulse duration in the range of 300-450 microseconds and the individual pulse frequency in the range of 2.2-3.3 kHz; and
repeating the causing of the first and second alternating currents for a plurality of iterations to provide a continuously pulsed time-varying magnetic field that alternates between the first and the second waveform frequencies, wherein the first length of time is between 2-12 seconds, and the second length of time is between 2-12 seconds, and the plurality of iterations is between 10-140 iterations, thereby generating a treatment session having a length of between 100-1000 seconds;
cause, based on receiving the parameters, a third alternating current having one or more third pulses to flow through the coil for a third length of time according to the third waveform frequency, thereby generating a recovery session, wherein each of the one or more third pulses has the pulse duration in the range of 300-450 microseconds and the individual pulse frequency in the range of 2.2-3.3 kHz, and the third length of time is between 30-80 seconds; and
generate a plurality of the treatment sessions, a pair of adjacent treatment sessions being separated by the recovery session;
wherein the first, second, and third waveform frequencies provide a continuously pulsed time-varying magnetic field that alternates between the first, second and third waveform frequencies, and wherein a magnetic flux density generated by the magnetic muscle stimulation device is between 1.2-2.0 tesla (T), an inductance of the coil is between 30-50 micro Henry (mH), and the coil has an inner diameter between 0-50 mm and an outer diameter of between 50-150 mm.

14. A method for strengthening, toning, and firming muscle tissues, the method comprising:
providing a magnetic muscle stimulation device, the magnetic muscle stimulation device comprising an applicator having a coil positioned in a housing of the applicator, an axis of the coil substantially perpendicular to an applicator surface of the housing;
causing a first alternating current to flow through the coil for a first length of time according to a first waveform frequency;
causing, following the first alternating current, a second alternating current to flow through the coil for a second length of time according to a second waveform frequency; and
repeating the causing of the first and second alternating currents for a plurality of iterations to provide a continuously pulsed time-varying magnetic field that alternates between the first and the second waveform frequencies, wherein one or more pulse durations of the first and second alternating currents is between 300-450 microseconds, each of the one or more pulse durations corresponding to a pulse frequency between 2.2-3.3 kHz, wherein the first waveform frequency is in the range of 10-50 Hz, the second waveform frequency is in the range of 2-10 Hz, the first length of time is between 2-12 seconds, the second length of time is between 2-12 seconds, and the plurality of iterations is between 10-140 iterations, thereby generating a treatment session having a length of between 100-1000 seconds, and wherein a magnetic flux density generated by the magnetic muscle stimulation device is between 1.2-2.0 tesla (T), an inductance of the coil is between 30-50 micro Henry (mH), and the coil has an inner diameter between 0-50 mm and an outer diameter of between 50-150 mm.

\* \* \* \* \*